(12) United States Patent
Hermansen et al.

(10) Patent No.: US 9,636,314 B2
(45) Date of Patent: May 2, 2017

(54) MEDICAMENT FOR TREATMENT OF NON-INSULIN DEPENDENT DIABETES MELLITUS, HYPERTENSION AND/OR METABOLIC SYNDROME

(71) Applicant: Stevia Limited, London (GB)

(72) Inventors: Kjeld Hermansen, Ega (DK); Soren Gregersen, Ega (DK); Per Bendix Jeppesen, Ega (DK)

(73) Assignee: Stevia Limited, London (GB)

(*) Notice: Subject to any disclaimer, the term of this patent is extended or adjusted under 35 U.S.C. 154(b) by 99 days.

(21) Appl. No.: 13/917,032

(22) Filed: Jun. 13, 2013

(65) Prior Publication Data

US 2014/0094408 A1   Apr. 3, 2014

Related U.S. Application Data

(60) Continuation of application No. 12/187,487, filed on Aug. 7, 2008, now abandoned, which is a continuation of application No. 11/819,659, filed on Jun. 28, 2007, now abandoned, which is a continuation of application No. 10/933,297, filed on Sep. 3, 2004, now abandoned, which is a division of application No. 10/210,787, filed on Jul. 31, 2002, now abandoned, which is a continuation of application No. PCT/DK01/00075, filed on Feb. 1, 2001.

(51) Int. Cl.
| | |
|---|---|
| *A61K 31/19* | (2006.01) |
| *A61K 31/015* | (2006.01) |
| *C07C 13/68* | (2006.01) |
| *A61K 31/192* | (2006.01) |
| *A61K 31/352* | (2006.01) |
| *A61K 31/70* | (2006.01) |
| *A61K 31/704* | (2006.01) |
| *A61K 36/00* | (2006.01) |
| *A61K 36/48* | (2006.01) |
| *A61K 38/16* | (2006.01) |
| *A61K 45/06* | (2006.01) |
| *C07C 61/35* | (2006.01) |
| *C07H 15/256* | (2006.01) |

(52) U.S. Cl.
CPC .......... *A61K 31/19* (2013.01); *A61K 31/015* (2013.01); *A61K 31/192* (2013.01); *A61K 31/352* (2013.01); *A61K 31/70* (2013.01); *A61K 31/704* (2013.01); *A61K 36/00* (2013.01); *A61K 36/48* (2013.01); *A61K 38/16* (2013.01); *A61K 38/168* (2013.01); *A61K 45/06* (2013.01); *C07C 13/68* (2013.01); *C07C 61/35* (2013.01); *C07H 15/256* (2013.01); *C07C 2103/86* (2013.01)

(58) Field of Classification Search
None
See application file for complete search history.

(56) References Cited

U.S. PATENT DOCUMENTS

| | | | | |
|---|---|---|---|---|
| 4,626,441 | A | 12/1986 | Wolkstein | 426/548 |
| 5,545,414 | A * | 8/1996 | Behr et al. | 424/484 |
| 5,980,902 | A * | 11/1999 | Shanmugasundaram et al. | 424/774 |
| 6,482,448 | B2 * | 11/2002 | Tabor | 424/757 |
| 7,091,183 | B1 * | 8/2006 | Wolfe et al. | 514/6.7 |
| 2003/0113390 | A1 * | 6/2003 | Hoie | 424/757 |
| 2010/0041598 | A1 | 2/2010 | Chen | |
| 2010/0093861 | A1 * | 4/2010 | Hermansen et al. | 514/557 |

FOREIGN PATENT DOCUMENTS

| | | |
|---|---|---|
| CA | 2 762 121 | 8/2001 |
| CN | 1195486 A | 10/1994 |
| CN | 1094580 A | 11/1994 |
| CN | 1148476 | 4/1997 |
| CN | 1154857 A | 7/1997 |
| EP | 0565785 A | 10/1993 |
| EP | 2 330 092 | 6/2011 |
| JP | 06-157302 | 6/1994 |
| JP | 7031407 | 2/1995 |
| JP | 08 325 156 A | 10/1996 |
| JP | 09052825 | 2/1997 |
| JP | 63 146813 A | 6/1998 |
| JP | 2002-500677 | 1/2002 |
| WO | WO 01/56959 | 8/2001 |
| WO | WO 02/060419 | 8/2002 |
| WO | WO 2006/116815 | 11/2006 |
| WO | 2008/031439 | 3/2008 |

OTHER PUBLICATIONS

Jeppesen et al., "Stevoside and Steviol Stimulate Insulin Secretion from Isolated Mouse Islets" Diabetologia (1996) vol. 39 suppl. A125.*
Elks et al., "Central Adiposity, Systemic Inflammation, and the Metabolic Syndrome" Curr Hypertens Rep (2010) pp. 1-10.*
Hansen, "The metabolic syndrome X" Annals of the New York Academy of Sciences (1999) vol. 892, pp. 1-24.*
Vedavanam et al., "Antioxidant Action and Potential Antidiabetic Properties of an Isoflavonoid-containing Soyabean Phytochemical Extract (SPE)" Phytotherapy Research (1999) vol. 13 pp. 601-608.*
Merriam-Webster's Collegiate Dictionary, Tenth Edition, published 1998 by Merriam-Webster, Incorporated, pp. 924 and 935.*
The Merck Manual of Diagnosis and Therapy, Seventeenth Edition, published 1999 by Merck Research Laboratories, p. 169.*
Malaisse et al., "Effects of Artificial Sweeteners on Insulin Release and Cationic Fluxes in Rat Pancreatic Islets" Cell Signal. (1998) vol. 10 No. 10, pp. 727-733.*
Merck Manual of Medical Information, Home Edition, 1997, p. 794-795.*
Merck Manual of Medical Information, Home Edition, 1997, p. 788.*
Macho et. al. Endocrine Regulations (34), 119-126, 2000.*
P.B. Jeppesen, et. al. Diabetologie, 1996, 39, Suppl. A125.*
Toskulkao, C. et. al. Toxicology Letters, 1995, 80, 153-159.*
Ponssen, HH, et. al. Clinical Therapeutics, 2000, 22, 709-718.*
DeFronzo, RA, et. al. Journal of Diabetes and Its Complications, 1996, 10, 243-245.*
Curi, et al., Effect of Stevia Rebaudiana on Glucose Tolerance in Normal Adult Humans, Brazilian J. Med. Biol. Res., 1986, pp. 771-774, vol. 19.

(Continued)

*Primary Examiner* — Eric Olson
(74) *Attorney, Agent, or Firm* — Browdy and Neimark, P.L.L.C.

(57) ABSTRACT

A dietary supplement or medicament comprising a substance including the chemical structure of bicyclo [3.2.1]octan or the chemical structure of kaurene. The medicament is useful for the treatment of non-insulin dependent diabetes mellitus, hypertension and/or the metabolic syndrome. The possible substances include steviol, isosteviol or stevioside.

13 Claims, 13 Drawing Sheets

(56) References Cited

OTHER PUBLICATIONS

Suanarunsawat, et al., The effect of stevioside on glucose metabolism in rat, Can. J. Physiol. Pharmacol., 1997, pp. 976-982, vol. 75.
Yamamoto, et al., Effect of steviol and its structural analogues on glucose production and oxygen uptake in rat renal tubules, Experientia, 1985, pp. 55-57, vol. 41.
Pezzuto, et al., "Metabolically activated steviol, the aglycone of stevioside, is mutagenic", Proc. Natl. Acad. Sci. USA, vol. 82, pp. 2478-2483, Apr. 1985.
Toskulkao, et al., "Effects of Stevioside and Steviol on Intestinal Glucose Absorption in Hamsters", J. Nutr. Sci. Vitaminol., vol. 41, pp. 105-113, 1995.
Wingard, et al., "Intestinal degradation and absorption of the glycosidic sweeteners stevioside and rebaudioside A[1]", Experientia, vol. 36, pp. 519-520, 1980.
Adams MR, et al. Soy Protein containing isoflavones reduces the size of atherosclerotic plaques without affecting coronary artery reactivity in adult male monkeys. J Nutr.; 135(12):2856-6 (Dec. 2005).
Ahlgren U, et al. Beta-cell-specific inactivation of the mouse 1pf1/Pdx1 gene results in loss of the beta-cell phenotype and maturity onset diabetes. Genes Dev.; 12(12):1763-8 (Jun. 15, 1998).
Bazargan et al. Determination of isosteviol by LC-MSMS and its application for evaluation of pharmacokinetics of isosteviol in rat DARU, vol. 15, No. 3. pp. 146-150 (2007).
Bergman RN, et al. The minimal modeling method. Methods in diabetes research, vol. II: Clinical Methods. Part B; 15-34, (1986).
Blair R.M., et al. Dietary soy and soy isoflavones have gender-specific effects on plasma lipids and isoflavones in golden Syrian f(1)b hybrid hamsters. J Nutr.; 132(12): 2585-91 (Dec. 2002).
Bruley C. et al. A novel promoter for the 11 beta-hydroxysteroid dehydrogenanse type 1 gene is active in lung and is C/EBPalpha independent. Endocrinology; 147: 2879-85 (2006).
Cardoso et al. Pharmacokinetic studies of stevioside and its metabolites. Nuclear Medicine and Biology, vol. 23, pp. 97-100 (1996).
Chang J.C. et al. Increase of insulin sensitivity by stevioside in fructose-rich chow-fed rats. Horm. Metab Res; 37: 610-16 (2005).
Chen J, et al. Stevioside improves pancreatic Beta-cell function during glucotoxicity via regulation of acetyl-CoA carboxylase. Am J Physiol Endocrinol Metab 292, E1906-E1916.(2007).
Chen T-H, et al. Mechanism of the hypoglycemic effffect of stevioside, a glycoside of stevia rebaudiana. Planta Med, 71: 108-113 (2005).
Edlund H. Transcribing pancreas; Diabetes; Dec; 47(12):1817-23 (1998).
Gardana C. et al. Metabolism of stevioside and rebaudioside a from stevia rebaudiana exracts by human microflora. J. Agric. Food Chem., 51, 6618-6622 (2003).
Geuns JMC, et al. Metabolism of stevioside in pigs and intestinal absorption characteristics of stevioside, rebaudioside A and steviol. Food and Chemical Toxicology, 41, 1599-1607 (2003).
Gregersen S, et al. Antihyperglycemic effects of stevioside in type 2 diabetic subjects. Metabolism, vol. 53, No. 1, pp. 73-76 (Jan. 2004).
Habener J. F., et al. Mini review: transscriptional regulation in pancreatic development. Endocrinology; 146: 1025-34 (2005).
Hansen L., et al. Missense Mutations in the Human Insulin Promotoer Factor-1 Gene and Their Relation to Maturity-Onset Diabetes of the Young and Late-Onset Type 2 Diabetes Mellitus in Caucasians. J. Clin. Endocrinol. Metab.; 85, 1323-1326 (2000).
Heding L.G. Determination of total serum insulin (iRI) in insulin-treated diabetic patients. Diabetologia; 8: 260-66 (1972).
Henseleit K.D., et al. NKX6 transcription factor activity is required for alpha- and beta-cell development in the pancreas. Development; 132: 3139-49 (2005).
Hermansen K., et al. Beneficial effects of a soy-based dietary supplement on lipid levels and cardiovascular risk markers in type 2 diabetic subjects. Diabetes Care; 24(2): 228-33 (2001).

Hsieh M-H, et al. Efficacy and tolerability of oral stevioside in patients with mild essential hypertension: a two-year, randomized, placebo-controlled study. Clinical Therapeutics, vol. 25, No. 11, pp. 2797-2808 (2003).
Ishii EL, et al. Inhibition of monosaccharide transport in the intact rat liver by stevioside. Biochemical Pharmacology. vol. 36, No. 9, pp. 1417-1433, (1987).
Kruhoffer M., et al. Gene expression signatures for colorectal cancer microsatetellite status and HNPCC. Br J. Canser 92: 2240-48 (2005).
Mach F. Inflammation is a crucial feature of atherosclerosis and a potential target to reduce cardiovascular events. Handb Exp Pharmacol. (170):697-722 (2005).
Malecki M.T., et al. Mutations in NEURODI1 are associated with the development of type 2 diabetes mellitus. Nat. Genet; 23: 223-28 (1999).
McGarry J.D. Dysregulation of Fatty Acid Metabolism in the Etiology of Type 2 Diabetes. Diabetes; 51 (1): 7-18 (2002).
Reusch J.E.B., and Klemm D.J. Editorial: Nutrition and Fat Cell Differentiation. Endocrinology; vol. 140, No. 7, pp. 2935-2937 (1999).
Saltiel, A.R. New Perspectives into the Molecular Pathogenesis and Treatment of Type 2 Diabetes. Cell; 104, 517-529 (2001).
Storlien L.H., et al. Influence of dietary fat composistion on development of insulin resistance in rats. Relationship to muscle triglyceride and -3 fatty acids in muscle phospholipids. Diabetes; 40:280-289 (1991).
Tolis G., et al. Medical treatment of acromegaly: comorbidities and their reversiblility by smatostatin analogs; Neuroendocrinology. 83: 249-57 (2006).
Usala A.L., et al. Brief report: Treatment of insulin-resistant ketoacidosis with insulin-like growth factor I in an adolescent with insulin diabetes. N Engl J Med.; 327-853-7 (1992).
Definition of medicine and medicament by American Heritage Dictionary, Second Edition, 1982, p. 781.
Berrs, M., The Merck Manual of Diagnosis and Therapy (17th ed) 1999, pp. 1654-1657.
Jeppsesen et al., "Stevioside Acts Directly on Pancreatic β Cells to Secrete Insulin: Actions Independent of Cyclic Adenosine Monophosphate and Adenosine Triphosphate-Sensitive K +-Channel Activity," Metabolism, vol. 29, No. 2, pp. 208-214 (2000).
Fuller et al., "HIV-inhibitoy natural products 28, Diterpene Carboxylic acid from fruits of xylopis SP," Natural Product letters, vol. 8, pp. 169-172, (1996).
M.S. Melis; "Stevioside effect on renal function of normal and hypertensive rats," Journal of Ethnopharmacology, vol. 36, pp. 213-217, (1992).
E. Fujita et al., "antitumor activity of the isodon diterpenoids: structural requirements for the activity," Experientia, vol. 32, No. 2, pp. 203-206, (1976).
Fuji et al., "Terpenoids L1) antitumor activity of diterpenoids from rabdosia shikokiana var. occidentals," Chem. Pharm. Bull., vol. 33, No. 3, pp. 1038-1042 (1985).
J.C. Craig et al., "Isolation and indentification of the hypoglycemic agent, carobxyatractylate, from Xanthium Sturnarium", Phytochemistry, vol. 15, p. 1178 (1976).
Lin Qixian et al., Abstract 158682, "Pilot experiment of extraction of stevioside," Zhongguo yiyao Gongye Zashi, vol. 22. No. 9, pp. 389-390, (1992).
Han Koo Dong et al., Abstract 468174, "Studies on diterpenoids from Siegesbeckia pubescens makino I. Diterpenes with Kaurane skeleton", Haksurwon Nommunjip, Cha 'Yon Kwahak P'Yon, vol. 12, pp. 171-183, (1973).
Han Koo Dong et al., Abstract 150777, "Chemistry and pharmacology of diterpenoids of Siegesbeckia pubescens", Yakhak Hoe Chi, P'Yon, vol. 19, No. 3, pp. 129-143, (1975).
Zhang Yu et al., Abstract 405267, "Protective effects of diterpenoid compounds on liver mitochondris injury induced by free radicals" Zhongguo Yaolixue Tongbao, vol. 15. No. 1, pp. 45-48, (1999).
Chiari Egler, Abstract 296922, "Chemoprophylaxis in Chagas' disease: potential use of natural products of plant origin and related synthetic compounds," Ciene Cult. vol. 48, No. 4, pp. 230-231, (1996).

(56) References Cited

OTHER PUBLICATIONS

Yong et al., Abstract 185140, "In vitro antitumor activity of diterpenes from Aralia cordata," Arch. Pharmacal Res., vol. 19, No. 1, pp. 77-78 (1996).
Chun-Fen et al., Abstract 25867, "Diacetylamethystoidin A protects isolated working rat heart against myocardial reperfusion injury." Zhonggua Yaoli Xuebao. col. 17, No. 3, pp. 245-248, (1996).
Lin Xu et al., Abstract 320960, "Preparation and clinical application of nutritional mixture," Guangdond Weilinang Yuansu Kexue, vol. 4, No. 9, pp. 56-60, (1997).
Abstract—Malaisse et al., "Effects of artificial sweeteners on insulin release and catonic fluxes in rat pancreatic islets," Cell signal, vol. 10, pp. 727-733, (1998).
Abstract: P. Chan et al., "The effect of stevioside on blood pressure and plasma catecholamines in spontaneously hypertensive rats," Life Sci. vol. 63 pp. 1679-1684, (1998).
Abstract: "Pilot experiment of extraction of Stevioside," Zhongguo Yiyao, vol. 22, No. 9, pp. 389-390, (1991).
Soejarto et al. Ethnobotanical notes on Stevie. Botanical Museum Leaflets: Harvard University, 1983, 29(1), 1-25.
Suanarunsawat et al. The effect of stevioside on glucose metabolism in rat. Can.J.Pharmacol., 1997, 75(8), 976-982.
Usami et al. Effect of cyclamate sodium, saccharin sodium and stevioside on arginine-induced insulin and glucagon secretion in the isolated perfused rat pancreas. Horm. Metab. Res., 1980, 12(12), 705-706.
Yu-Wan Cheng. Antihypertensive effect of Isosteviol (ST-1). National Cheng Kung University Graduate Institute of Pharmacology Masters Thesis. Jun. 22, 1999, 1-61.
Xiufang, Liu, "Experiment on Modification and Bioactivity of Steviol-type bonding", *Journal of Wuhan University (Natural Science Edition)*, vol. 2, No. 2, pp. 74-78, 1994.
Anderson J.W. et al.; Meta-analysis of the effects of soy protein intake on serum lipids. N. Engl. J. Med. 1995; 333: 276-282.
Bridel m., et al. Le Principe a sucree du Kaa-he-e, Soc Chim Biol Paris, vol. 13, pp. 636-656, 1931.
Chen, J. et al.; Stevioside does not cause increased basal insulin secretion or β-cell desensitization as does the sulphonylurea, glibenclamide: studies in vitro; Life Sciences; 2006; 1748-1753.
Curi R., et al.; Effect of Stevia rebaudiana on glucose tolerance in normal adult humans. Braz. J. Med. Biol. Res., 19, p. 771-774,1986.
Dyrskog, S. E. U. et al.; Preventive effects of a soy-based diet supplemented with stevioside on the development of the metabolic syndrome and type 2 diabetes in zucker diabetic fatty rats; Metabolism Clinical and Experimental; 54; 2005; 1181-1188.
Geuns, J.M.C. et al.; Identification of steviol glucuronide in human urine; J. Agric. Food Chem.; 2006; 54; 2794-2798.
Geuns, J.M.C. et al.; Metabolism of stevioside by healthy subjects; Experimental Biology and Medicine; 2007; 232:164-173.
Hansson J.R., et al.; Stevioside and related sweet diterpenoid glycoside. Nat. Prod. Rep. 21, p. 301-309, 1993.
Hong, J. et al.; Stevioside counteracts the alfa-cell hypersecretion caused by long-term palmitate exposure. Am J Physiol Endocrinol Metab; 2006;290; E416-E422.
International Diabetes Foundation, "The IDF consensus worldwide definition for the metabolic syndrome", 2006 (brochure).
Ishii-Iwamoto E.L., et al.; Stevioside is not metabolised in the isolated perfused rat liver. Res. Commun. Mol. Pathol. Pharmacol. Feb. 1995;87(2), p. 167-75.
Jeppesen, P. B. et al.; Antihyperglycemic and blood pressure-reducing effects of stevioside in the diabetic goto-kakizaki rat; Metabolism, vol. 52, No. 3, 2003, pp. 372-378.
Jeppesen, P. B. et al.; Can stevioside in combination with a soy-based dietary supplement be a new useful treatment in type 2 diabetes? An in vivo study in the diabetic goto-kakizaki rat; Rev Diabetic Stud ; 2006; 3; 189-199.
Jeppesen, P.B. et al.; Stevioside Acts Directly on Pancreatic Beta Cells to Secrete Insulin: Actions Independent of Cyclic Adenosine Monophosphate and Andeosine Triphosphate-Sensitive K+ -Channel Activity, Metabolism, vol. 49, No. 2, 2000: pp. 208-214.

Ju-Chi Liu et al.; The antihypertensive effect of stevioside derivative isosteviol in spontaneously hypertensive rats; Acta Cardiol Sin; 2001; 17; 133-140.
Klongpanichpak S. et al.; Lack of mutagenicity of stevioside and steviol in *Salmonella typhimurium* TA 98 and TA 100. J. Med. Assoc. Thai Sep. 1997 ;80 Suppl. 1, p. 121-128.
Kohda H., et al.; New sweet diterpene glucosides from Stevia rebaudiana. Phytochemistry 15, p. 981-983,1976.
Lebovitz H.E., 1997 The oral hypoglycemic agents. 1997 In: Ellenberg and Rifkin's Diabetes Mellitus. D.J. Porte and R.S. Sherwin, Editors: Appleton and Lange, p. 761-788.
Lun-Huei Lin et al.; Study of the stevioside analogues of steviolbioside, steviol, and isosteviol 19-alkyl amide dimers: synthesis and cytotoxic and antibacterial activity; Chem. Pharm. Bull.; 2004; 52(9) 1117-1122.
Ma J. et al.; Isosteviol reduces plasma glucose levels in the intravenous glucose tolerance test in zucler diabetic fatty rats; Diabetes, obesity and metabolism; 0, 2006, 1-3.
Matsui M., et al.; Evaluation of the genotoxicity of stevioside and steviol using six in vitro and one in vivo mutagenicity assays. Mutagenesis Nov. 1996;11(6), p. 573-579.
Melis M.S.; "Renal excretion of stevioside in rats". J. Nat. Prod. May 1992;55(5), p. 688-90.
Mossettig E., et al.; II: "The structure of the aglucone"; J. Org. Chem. 20, p. 884-899,1955.
Oviedo C.A., et al.; Action hipoglucemiante de la Stevia Rebaudiana Bertoni (Kaa-he-e). Excerpt. Med. 209, p. 92,1979.
Pezzuto, John M.; Chemistry, Metabolism and Biological Activity of Steviol (ENT-13-Hydroxykaur-16-EN-19-OIC Acid), The Aglycone of Stevioside. Studies in Organic Chemistry, Elsevier, Amsterdam, NL., vol. 26, 1986, pp. 371-386.
Sakaguschi M.; Kan P Aspesquisas japonesas corn Stevia rebaudiana (Bert) Bertoni e o estevioside. Cienc. Cultur. 34; 235-248:1982.
Soejarto, et al., Potential Sweetening Agents of Plant Origin. II. Field Search for Sweet-Tasting Stevia Species, Economic Botany, vol. 37(1), pp. 71-79, 1983.
Srimaroeng, C. et al.; Transport of the natural sweetener stevioside and its aglycone steviol by human organic anion transporter (hOAT1; SLCA6) and hOAT3 (SLC22A8); J Pharmacol Experimental Therapeutics; 313; 2; 621-628, (2005).
Suttajit M. et al.; Mutagenicity and human chromosomal effect of stevioside, a sweetener from Stevia rebaudiana Bertoni. Environ Health Perspect Oct. 1993;101 Suppl. 3, p. 53-56.
Toskulkao C. et al.; Acute toxicity of stevioside, a natural sweetener, and its metabolite, steviol, in several animal species. Drug Chem. Toxicol. Feb.-May 1997;20(1-2), p. 31-44.
Toskulkao, C. et al.; Inhibitory effect of a steviol, a metabolite of stevioside, on glucose absorption in everted hamster intestine in vitro. Toxicology Letters 80 (1995) 153-159.
Toyoda K., et al.; Assessment of the carcinogenicity of stevioside in F344 rats. Food Chem. Toxicol. Jun. 1997;35(6), p. 597-603.
WHO; Definition, Diagnosis and Classification of Diabetes Mellitus and its Complications. 1999. WHO Report WHO/NCD/NCS/99.2.
Yodyingyuad V., et al.; Effect of stevioside on growth and reproduction. Hum. Reprod. Jan. 1991;6(1), p. 158-165.
Adrian, et al., "Pancreatic polypetpide, glucagon and insulin secretion from the isolated perfused canine pancreas", *Diabetologia*, vol. 14 (6), pp. 413-417, Jun. 1978.
Alstrup, et al., "Long-Term exposure of INS-1 cells to cis and trans fatty acids influences insulin release and fatty acid oxidation differentially", *Metabolism*, vol. 53(9), pp. 1158-1165, Sep. 2004.
Arcaya, et al., "Effect of adrenomedullin and proadrenomedullin N-terminal 20 peptide on sugar transport in the rat intestine", *Regulatory Peptides*, vol. 129, pp. 147-154, 2005.
Cermak, et al., Abstract Only, "Quercetin glucosides inhibit glucose uptake into brush-border-membranse vesicles of porine jejunum", *Br J Nutr.*, vol. 91 (6), pp. 849-855, Jun. 2004.
Chen, et al., "Interaction of Flavonoids and Intestinal Facilitated Glucose Transporters", *Planta Med*, vol. 73, pp. 348-354, 2007.

(56) References Cited

OTHER PUBLICATIONS

Chen, et al., "Stevioside does not cause increased basal insulin secretion or β-cell desensitization as does the sulphonylurea, glibenclamide: studies in vitro", *Life Sciences*, vol. 78(15), pp. 1748-1753, Mar. 2006.

Chopra, et al., Abstract Only, "Intestinal toxicity of non-steroidal anti- inflammatory drugs with differential cyclooxygenase inhibition selectivity", *Nutr Hosp.*, vol. 22(5), pp. 528-537, Sep.-Oct. 2007.

Dunning, et al., Abstract Only, "The presence and action of NPY in the canine endocrine pancreas", *Requl Pept.*, vol. 18(5-6), pp. 253-265, Sep. 1987.

Dyrskog et al., "Preventive effects of a soy-based diet supplemented with stevioside on the development of the metabolic syndrome and type 2 diabetes in Zucker diabetic fatty rats", *Metabolism Clinical and Experimental*, vol. 54, pp. 1181-1188, 2005.

European Food Safety Authority (EFSA), Parma, Italy, "Scientific Opinion on the safety of steviol glycosides for the proposed uses as a food additive", *EFSA Journal*, vol. 8(4), pp. 1537-1539, 2010.

Fery, et al., Abstract Only, "Effect of Somatostatin on Duodenal Glucose Absorption in Man", *J Clin Endocrinol Metab.*, vol. 90(7), pp. 4163-4169, 2005.

Hales et al., "Cations and the secretion of insulin from rabbit pancreas in vitro", *J Physiol*, vol. 199(1), pp. 177-187, Nov. 1968.

Hermansen, K., "Effects of Substance P and Other Peptides on the Release of Somatostatin, Insulin, and Glucagon in Vitro", *Endocrinology*, vol. 107, No. 1, pp. 256-261, 1980.

Hermansen, K., "Effects of Cholecystokinin (CCK)-4, Nonsulfated CCK-8, and Sulfated CCK-8 on Pancreatic Somatostatin, Insulin and Glucagon Secretion in the Dog: Studies in Vitro", *Endocrinology*, vol. 114, No. 5, pp. 1770-1775, 1984.

Hermansen K., "Effects of galanin on the release of insulin, glucagon and somatostatin from the isolated, perfused dog pancreas", *Acta Endocrinol (Copenh)*, vol. 119(1), pp. 98-98, Sep. 1988.

Hermansen, K., "Enkephalins and the secretion of pancreatic somatostatin and insulin in the dog: studies in vitro", *Endocrinology*, vol. 113(3), pp. 1149-1154, Sep. 1983.

Hermansen, K., "Effects of a thiazide diuretic (hydroflumethiazide) and a loop diuretic (bumetanide) on the endocrine pancreas: studies in vitro", *Metabolism*, vol. 34(8), pp. 784-789, Aug. 1985.

Hermansen, et al., "Synthetic pancreatic growth hormone-releasing factor (GRF-40) stimulates the secretion of the endocrine pancreas", *Diabetes*, vol. 35(1), pp. 119-123, Jan. 1986.

Hermansen, et al. "Gastrin releasing peptide stimulates the secretion of insulin, but not that of glucagon or somatostatin, from the isolated perfused dog pancreas", *Acta Physiol Scand*, vol. 138(2), pp. 175-179, Feb. 1990.

Hermansen, et al., "Characterisation of somatostatin release from the pancreas: the role of calcium and acetylocholine", *Diabetologia*, vol. 16(4), pp. 261-266, Apr. 1979.

Hermansen, K, "Stimulatory effect of beta-hydroxybutyrate on the release of somatostatin from the isolated pancreas of normal and streptozotocin-diabetic dogs", *Diabetes*, vol. 31(3), pp. 270-274, Mar. 1982.

Hermansen K., "Secretion of somatostatin from the normal and diabetic pancreas. Studies in vitro", *Diabetologia*, vol. 19(6), pp. 492-504, 1980.

Lee, et al., "Potential impact of chemical prophylaxis on the incidence of gonorrhoea", *Brit. J. Vener. Dis.*, vol. 48, pp. 376-380, 1972.

Milner, et al., "The interaction of various inhibitors and stimuli of insulin release studied with rabbit pancreas in vitro", *Biochem J.*, vol. 113(3), pp. 473-479, Jul. 1969.

Stein, et al., "The insulinotropic potency of fatty acids is influenced profoundly by their chain length and degree saturation"*J Clin Invest.*, vol. 100(2), pp. 298-403, Jul. 1997.

Usami, et al., "Effect of Cyclamate Sodium, Saccharin Sodium and Stevioside on Arginine-Induced Insulin and Glucagon Secretion in the Isolated Perfused Rat Pancreas", *Horm. Metab. Res.*, vol. 12, pp. 705-806, 1980.

Weir, et al., "Somatostatin pancreatic polypeptide secretion: effects of glucagon, insulin, and arginine" *Diabetes*, vol. 28, No. 1, pp. 35-40, Jan. 1979.

Yamamoto, et al., Abstract Only, "Gastrointestinal uptake of FDG after N-butulscopolamine or omeprazole treatment in the rat", *Ann Nucl Med.*, vol. 18(7), pp. 634-640, Oct. 2004.

Merriam-Webster, "prophylactic", Free Merriam-Webster Dictionary, http://www.merriam-webster.com/dictionary/prophylactic, Accessed Nov. 9, 2010.

MSN, "prophylactic", Encarta, http://encarta.msn.com/dictionary_1861736495/prophylactic.html, Accessed Nov. 9, 2010.

Farlex, "prophylactic", The Free Dictionary, http://www.thefreedictionary.com/prophylactic, Accessed Nov. 9, 2010.

International SOS, "Pandemic Preparedness", http://www.internationalsos.com/pandemicpreparedness/SubCatLevel.aspx?li=5&languageID=Eng&subCatID=19, Accessed Nov. 9, 2010.

Princeton University, "Prophylactic", WordNet, http://wordnetweb.princeton.edu/perl/webwn?s=prophylactic&sub=Search+WordNet& o2=&o0=1&o7=&o5=&o1=1&o6=&o4=& o3=&h=, Accessed Nov. 16, 2010.

Avent et al; Hydrolysis of the diterpenoid glycoside, stevioside. Phytochemistry, vol. 29, No. 8, pp. 2712-2715 (1990).

Boeckh Haebisch, E. M. A.: "Pharmacological trial of a concentrated crude extract of stevia rebaudiana (Bert) Bertoni in healthy volunteers". Arquivos de Biologia e Tecnologia, Instituto de Tecnologia do Parana, Curitiba, BR, vol. 35, No. 2, Jun. 1, 1992, pp. 299-341.

Bracht, A. K. et al.: "Effects of stevia rebaudiana natural products on rat liver mitochondria". Biochemical Pharmacology, Pergamon, Oxford, GB, vol. 34, No. 6, Mar. 15, 1985, pp. 873-882.

Ishii and Brecht: "Glucose release by the liver under conditions of reduced activity of glucose 6-phosphatase"; Brazilian J Med Biol Res (1987) 20: pp. 837-843.

Kelmer Bracht, A. M. et al.: "Effect of stevia rebaudiana natural products on cellular and sub-cellular metabolism". Arq. Biol. Tecnol., vol. 28, No. 3, Jan. 1, 1985, pp. 431-455.

Kelmer Bracht, A. M. et al.: "Estudio cinético da inibicao da NADH-oxidase pelo isostevio e seus derivados". Revista Unimar, BR, vol. 6, No. 1, Jan. 1, 1984, pp. 151-167.

Melis, M. S.: "Effects of steviol on renal function and mean arterial pressure in rats". Phytomedicine, Gustav Fischer Verlag, Stuttgart, DE, vol. 3, No. 4, Jan. 1, 1997, pp. 349-352.

Melis, M.S.: "Chronic administration of aqueous extract of stevia rebaudiana in rats: renal effects". Journal of ethnopharmacology, vol. 47, 1995, pp. 129-134.

Oliveira-Filho, R. M. et al: "Chronic administration of aqueous extract of stevia rebaudiana (bert.) bertoni in rats: endocrine effects". General Pharmacology, Pergamon Press, Oxford, GB, vol. 20, No. 2, Jan. 1, 1989, pp. 187-191.

Ross et al; "Glucose metabolism in renal tubular function". Kidney Inernational, vol. 29 (1986), pp. 54-67.

Schmeling, G. A. von et al.: "Stevia rebaudiana bertoni: evaluation of the hypoglucemic effect in alloxanized rabits". Ciencia e Cultura, Rio de Janeiro, BR, vol. 29, No. 5, May 1, 1977, pp. 599-601.

Stumvoll et al; "Renal glucose production and utilization: new aspects in humans". Diabetologia (1997) 40: pp. 749-757.

Suzuki, H. et al.: "Influence of oral administration of stevioside on levels of blood glucose and liver glycogen on intact rats". Nippon Nogei Kagakukaishi—Journal of the Agricultural Chemical Society of Japan, Nippon Nogei Kagakukai, Tokyo, JP, vol. 51, No. 3, Jan. 1, 1977, pp. 171-173.

Tseng et al; Postprandial Stimulation of Insulin Release by Glucose-dependent Insulinotropic Polypeptide (GIP). J Clin. Invest, The American Society for Clinical Investigation, Inc., vol. 98, No. 11, Dec. 1996, pp. 2440-2445.

Wirthensohn et al; "Renal substrate metabolism". Physiological Reviews, vol. 66, No. 2, Apr. 1986, pp. 469-497.

Yamamoto et al.; "Effect of steviol and its structural analogues on glucose production and oxygen uptake in rat renal tubules"; Experientia 41:55-57, 1985.

\* cited by examiner

MEDICAMENT FOR TREATMENT OF NON-INSULIN DEPENDENT DIABETES MELLITUS, HYPERTENSION AND/OR METABOLIC SYNDROME

This application is a continuation of U.S. application Ser. No. 10/933,297 filed Sep. 3, 2004, which is a division of Ser. No. 10/210,787 filed Jul. 31, 2002, which is a continuation of PCT/DK01/00075 filed Feb. 1, 2001. The prior applications set forth above are hereby incorporated by reference in their entirety.

TECHNICAL FIELD

The present invention relates to a new medicament for the treatment of non-insulin dependent diabetes mellitus, hypertension, metabolic syndromes and other conditions in mammals.

BACKGROUND ART

Diabetes is a common disease that has a prevalence of 2-4% in the population. Non-insulin dependent diabetes mellitus comprises about 85% of diabetes most commonly occurring at the age above 40 years. The incidence of non-insulin dependent diabetes mellitus is increasing and is at a global level expected to surpass 200 million subjects at year 2010.

Diabetes is associated with increased morbidity and a 2-4-fold increase in mortality primarily due to cardiovascular diseases and strokes.

Non-insulin dependent diabetes mellitus develops especially in subjects with insulin resistance and a cluster of cardiovascular risk factors such as obesity, hypertension and dyslipidemia, a syndrome which first recently has been recognized and is named "The metabolic syndrome" (Alberti K. G., Zimmet P. Z.; Definition, diagnosis and classification of diabetes mellitus and its complications". Part 1: Diagnosis and classification of diabetes mellitus provisional report of a WHO consultation. Diabet. Med. 1998 July; 15 (7), p. 539-53).

In accordance with the WHO-definition (www.idi.org.au/whoreport.htm), a patient has metabolic syndrome if insulin resistance and/or glucose intolerance is present together with two or more of the following conditions:

reduced glucose tolerance or diabetes insulin sensitivity (under hyperinsulinaemic, euglycaemic conditions corresponding to a glucose uptake below the lower quartile for the background population)

increased blood pressure ($\geq 140/90$ mmHg)

increased plasma triglyceride ($\geq 1.7$ mmol/l) and/or low HDL cholesterol (<0.9 mmol/l for men; <1.0 mmol/l for women)

central adipositas (waist/hip ratio for men: >0.90 and for women>0.85) and/or Body Mass Index>30 kg/m$^2$)

micro albuminuria (urine albumin excretion: $\geq 20$ µg min$^{-1}$ or albumin/creatinine ratio$\geq 2.0$ mg/mmol.

It has become increasingly evident that the treatment should aim at simultaneously normalizing blood glucose, blood pressure, lipids and body weight to reduce the morbidity and mortality. Diet treatment, exercise and avoiding smoking are the first treatment modalities that should be started. However, it will often be necessary to add pharmacological therapy but until today no single drug that simultaneously attacks hyperglycaemia, hypertension and dyslipidemia are available for patients with metabolic syndrome. Instead, these patients may be treated with a combination of several different drugs in addition to e.g., diet. This type or treatment is difficult to adjust and administer to the patient and such treatment may result in many unwanted adverse effects which in themselves may need medical treatment.

Consequently there is a long felt need for a new and combined medicament for the treatment of metabolic syndrome thereby also preventing an increase in the number of persons developing the non-insulin dependent diabetes mellitus.

Existing oral antidiabetic medicaments to be used in such treatment include the classic insulinotropic agents sulphonylureas (Lebovitz H. E. 1997. "The oral hypoglycemic agents". In: Ellenberg and Rifkin's Diabetes Mellitus. D. J. Porte and R. S. Sherwin, Editors: Appleton and Lange, p. 761-788). They act primarily by stimulating the sulphonylurea-receptor on the insulin producing beta-cells via closure of the K$^+_{ATP}$-sensitive channels. However if such an action also affects the myocytes in the heart, an increased risk of cardiac arrhytmias might be present. Also, it is well know in the art that sulphonylureas can cause severe and lifethreatening hypoglycemia, due to their continuous action as long as they are present in the blood.

Consumption of soy protein rather than animal protein has been found to lower blood cholesterol (Anderson J. W., Johnstone B. M., Cook-Newell M. E.: Meta-analysis of the effects of soy protein intake on serum lipids. N. Engl. J. Med. 1995; 333; p. 276-282). In addition to this knowledge, recent research also provides evidence that soy protein and/or isoflavones may improve endothelial function and attenuate events leading to both lesion and thrombus formation (Anderson J. W., Johnstone B. M., Cook-Newell M. E.: "Meta-analysis of the effects of soy protein intake on serum lipids"; N. Engl. J. Med. 1995; 333; p. 276-282; Potter S. M., Soy protein and cardiovascular disease: "The impact of bioactive components in soy". Nutrition Reviews 1998; 56, p. 231-235).

Several attempts to develop new antidiabetic agents and drugs for the treatment or prophylactic treatment of the syndrome not having the adverse effects mentioned above, e.g. hypoglycemia and potential harmful actions on the heart functions have been made over the years. For this purpose, plants provide a vast resource of compounds with the potential to become new antidiabetic agents.

For instance extracts of the leaves of *Stevia rebaudiana* Bertoni, a herbaceous member of the Compositae family, have been used for many years in the treatment of diabetes among Indians in Paraguay and Brazil (Sakaguschi M., Kan P *Aspesquisas japonesas* com *Stevia rebaudiana* (Bert) Bertoni e o estevioside. Cienc. Cultur. 34; p. 235-248, 1982; Oviedo C. A., Franciani G., Moreno R., et al. "Action hipoglucemiante de la *Stevia Rebaudiana* Bertoni (Kaa-he-e)". Excerpt. Med. 209, p. 92, 1979; Curi R., Alvarez M., Bazotte R. B., et al. Effect of *Stevia rebaudiana* on glucose tolerance in normal adult humans. Braz. J. Med. Biol. Res., 19, p. 771-774, 1986; Hansson J. R., Oliveira B. H., "Stevioside and related sweet diterpenoid glycoside". Nat. Prod. Rep. 21, p. 301-309, 1993).

Also, an antihyperglycemic effect has been found in rats when supplementing the diet with dried *S. rebaudiana* leaves (Oviedo C. A., Franciani G., Moreno R., et al. "Action hipoglucemiante de la *Stevia Rebaudiana* Bertoni (Kaa-he-e)". Excerpt. Med. 209:92, 1979). Curi et al. found a slight suppression of plasma glucose when extracts of *Stevia rebaudiana* leaves were taken orally during a 3-day period. Furthermore, Oviedo et al. reported that tea prepared from the leaves caused a 35% reduction in blood glucose in man.

A number of *Stevia* species have been examined and shown to contain labdanes, clerodanes, kaurenes and beyerenes (Hansson J. R., Oliveira B. H., "Stevioside and related sweet diterpenoid glycoside". Nat. Prod. Rep. 21, p. 301-309, 1993). Any of these substances as well as many others unidentified substances in the leaves could be responsible for the reduction in blood glucose in man.

In the work of Malaisse W. J. et al (Malaisse W. J., Vanonderbergen A., Louchami K, Jijakli H. and Malaisse-Lagae F., "Effects of Artificial Sweeteners on Insulin Release and Cationic Fluxes in Rat Pancreatic Islets", Cell. Signal. Vol 10, No. 10, p. 727-733, 1998) the effect of several artificial sweeteners, including stevioside, on insulin release from isolated normal pancreatic rat islets were studied. In this study it was reported that in the presence of 7 mmol/l D-glucose, stevioside in a concentration of 1.0 mmol/l caused a significant increase in insulin output. Also the control group demonstrated a significant increase in insulin output of about 16 times above the basal release value in the presence of 20 mmol/l D-glucose increase. It is therefore uncertain whether the insulin releasing effect is due to the increased glucose level or the presence of stevioside. No diabetic islet cells were studied and the skilled person within the art will know that the mechanism for stimulating normal pancreatic islet cells either not functions at its optimum or not functions at all in the diabetic pancreatic cells, and that the study provided no certain indication of the possible use of stevioside in the treatment of non-insulin dependent diabetes mellitus, hypertension and/or the metabolic syndrome.

In a Chinese study (Lin Qi-Xian, Cao Hai-Xing, Xie Dong, Li Xing-Ming, Shang Ting-Lan, Chen Ya-Sen, Ju Rui-Fen, Dong Li-Li, Wang Ye-Wen, Quian Bao-Gong, "Experiment of Extraction of Stevioside", Chinese Journal og Pharmaceuticals 1991, No. 22, p 389-390) is indicated a method for extracting stevioside from stevioside leafs from the origin of Bingzzhou in the Hunan Province. The content of stevioside in the extract was determined using HPLC although the article is silent of the purity of the extract. The produced stevioside tablets were for no apparent reason and medical indication applied to patients in the Wuhan Second Hospital. No data on the influence of stevioside on blood glucose, insulin and/or blood pressure is revealed. It is stated that the tablets were effective to diabetes and hypertension during preliminary clinical observations. However, total lack of data on blood glucose, insulin and/or blood pressure i.e., lack of support by test results and the missing information of which types of diabetes that were treated, makes this an unsupported and unconfirmed assertion.

Any detailed information of which substance or substances in the leaves that might cause a possible anti-hyperglycemic effect has not yet been disclosed for certainty, and the mechanism of how and to which extent the plasma glucose is reduced is unknown. The above mentioned articles and studies are concerned with the initial discovery of the effects and provide no evidence of which specific component(s) in the leaves that might be the active one(s).

The effect of intravenous stevioside on the blood pressure was studied in spontaneously hypertensive rats ("The Effect of Stevioside on Blood Pressure and Plasma Catecholamines in Spontaneously Hypertensive Rats", Paul Chan, De-Yi Xu, Ju-Chi Liu, Yi-Jen Chen, Brian Tomlinson, Wen-Pin Huang, Juei-Tang Cheng, Life Science, Vol. 63, No. 19, 1998, p. 1679-1684). The study showed that during an intravenously administration of stevioside of 200 mg/kg the hypotensive effect was at a maximum, but although reported as being significantly the fall in the systolic blood pressure was only small. Neither the heart rate nor the plasma catecholamines were significantly changed during the observation period. This study indicated that stevioside advantageously could be used for treating hypertension.

No reports of an effect on plasma glucagon level have previously been reported. Glucagon, a pancreatic islet hormone, acts as a diabetogenic hormone by increasing the hepatic glucose output thereby elevating blood glucose.

Recent studies and tests made by the present inventors have focused on especially the diterpenoid glycoside stevioside which is a major constituent found in the leaves of *Stevia rebaudiana* where it may occur in amounts of up to about 10% (Hansson J. R., Oliveira B. H., "Stevioside and related sweet diterpenoid glycoside". Nat. Prod. Rep. 21, p. 301-309, 1993; Bridel M., Lavielle R., Physiologie Vegetale: "Sur le principe sucre'du Kaa' he'e (*Stevia rebaudiana* Bertoni): II Les produits d'hydrolyse diastasique du stevioside, glucose et steviol". Acad. Sci. Paris 192, p. 1123-1125, 1931; Soejarto D. D., Kinghorn A. D., Farnsworth N. R., Potential sweetening agent of plant origin. III: "Organoleptic evaluation of *Stevia* leaf herbarium samples for sweetness". J. Nat. Prod. 45, p. 590-598, 1983; Mossettig E., Nes W. E. Stevioside. II: "The structure of the aglucone"; J. Org. Chem. 20, p. 884-899, 1955; Kohda H., Hasai R., Yamasaki K. et al. "New sweet diterpene glucosides from *Stevia rebaudiana*". Phytochemistry 15, p. 981-983, 1976).

Also, its aglycone, steviol, has been found to be contained in the leaves of *Stevia rebaudiana* as well as other sweet-tasting glycosides e.g. Steviolbioside, Rebaudioside A,B, C,D and E, and Dulcoside (Bridel M., Lavielle R., Physiologie Vegetale: "Sur le principe sucre'du Kaa' he'e (*Stevia rebaudiana* Bertoni): II Les produits d'hydrolyse diastasique du stevioside, glucose et steviol". Acad. Sci. Paris 192, p. 1123-1125, 1931; Soejarto D. D., Kinghorn A. D., Farnsworth N. R., Potential sweetening agent of plant origin. III: "Organoleptic evaluation of *Stevia* leaf herbarium samples for sweetness". J. Nat. Prod. 45, p. 590-598, 1983; Mossettig E., Nes W. E. Stevioside. II: "The structure of the aglucone"; J. Org. Chem. 20, p. 884-899, 1955; Mossettig E., Nes W. E. Stevioside. II: "The structure of the aglucone"; J. Org. Chem. 20, p. 884-899, 1955; Kohda K., Hasai R., Yamasaki K. et al. "New sweet diterpene glucosides from *Stevia rebaudiana*". Phytochemistry 15, p. 981-983, 1976).

The present inventors have already successfully proved that both stevioside and steviol have an anti-hyperglycemic, glucagonostatic and insulinotropic effect when administered intravenously to rats and a stimulatory effect on the insulin secretion from mouse islets in vitro.

No well defined, chemical stable, non-toxic, reliable and non-adverse effects alternative to the sulphonylureas for the treatment of non-insulin dependent diabetes mellitus is available today, however, and these findings have given rise to further studies and tests of analogues and derivates of these substances in order to find improved and alternative drugs for a self-regulatory treatment of diabetes, hypertension and especially metabolic syndrome in mammals, and preferably in humans.

In order to prevent sequelae or to delay the developing of a number of the above-mentioned metabolic and functional disorders in humans, there is a need it for new and beneficial dietary supplementations or new self-administrable non-prescription drugs for prophylaxis. The present invention now satisfies this need.

SUMMARY OF THE INVENTION

Accordingly, the present invention relates to a selectively responsive medicament composition comprising at least one substance including a bicyclo [3.2.1]octan in a double ring system having a basic chemical skeletal of a kaurene structure having the structural formula II:

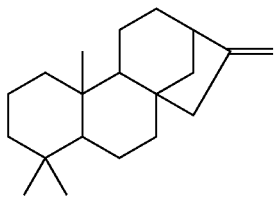 [SMILES: C=C1CC23CCC4C(C)(C)CCCC4(C)C2CCC1C3]

or an analogue, derivative or metabolite thereof, wherein the substance responds only at an elevated plasma glucose concentrations. Generally, the response of the substance is initiated by a plasma glucose concentration of 6 mmol/l or larger.

Preferably, the substance is selected from the group consisting of steviol, isosteviol, glucosilsteviol, gymnemic acid, steviolbioside, stevioside Rebaudioside A, Rebaudioside B, Rebaudioside C, Rebaudioside D, Rebaudioside E and Dulcoside A, their pharmaceutically acceptable analogues or their pharmaceutically acceptable derivates. The substance can be isolated from a plant source and can be used alone or in combination with at least one soy protein alone or in combination with at least one isoflavone.

The substance and composition can be used as a dietary supplement or as a medicament for a mammal. As noted above the substance or composition is responsive in the mammal only when the mammal's plasma glucose concentrations are elevated. Thus, the medicament can be used for treating the mammal for non-insulin dependent diabetes mellitus, metabolic syndrome, to stimulate insulin production, to reduce glucagon concentrations, to suppress fasting plasma triglycerides or total cholesterol levels in the mammal, or for treating hypertension in the mammal. Preferably, the medicament is an oral medicament and is self-regulating.

The invention also relates to a method of making a selectively responsive composition which comprises associating with a carrier a bicyclo [3.2.1]octan in a double ring system having a basic chemical skeletal of a kaurene structure having the structural formula II, wherein the substance responds only at an elevated plasma glucose concentrations. The composition that is made can be used as a dietary supplement or as one of the medicaments mentioned above.

The invention also relates to various treatment methods for mammals, including treating non-insulin dependent diabetes mellitus, treating metabolic syndrome, treating hypertension, suppressing fasting plasma triglycerides, suppressing total cholesterol level, or suppressing appetite.

BRIEF DESCRIPTION OF THE DRAWINGS

The invention is further illustrated by the following examples and the accompanying drawings that are intended to illustrate preferred features and properties of the invention, wherein.

DETAILED DESCRIPTION OF THE PREFERRED EMBODIMENTS

Figure 1:
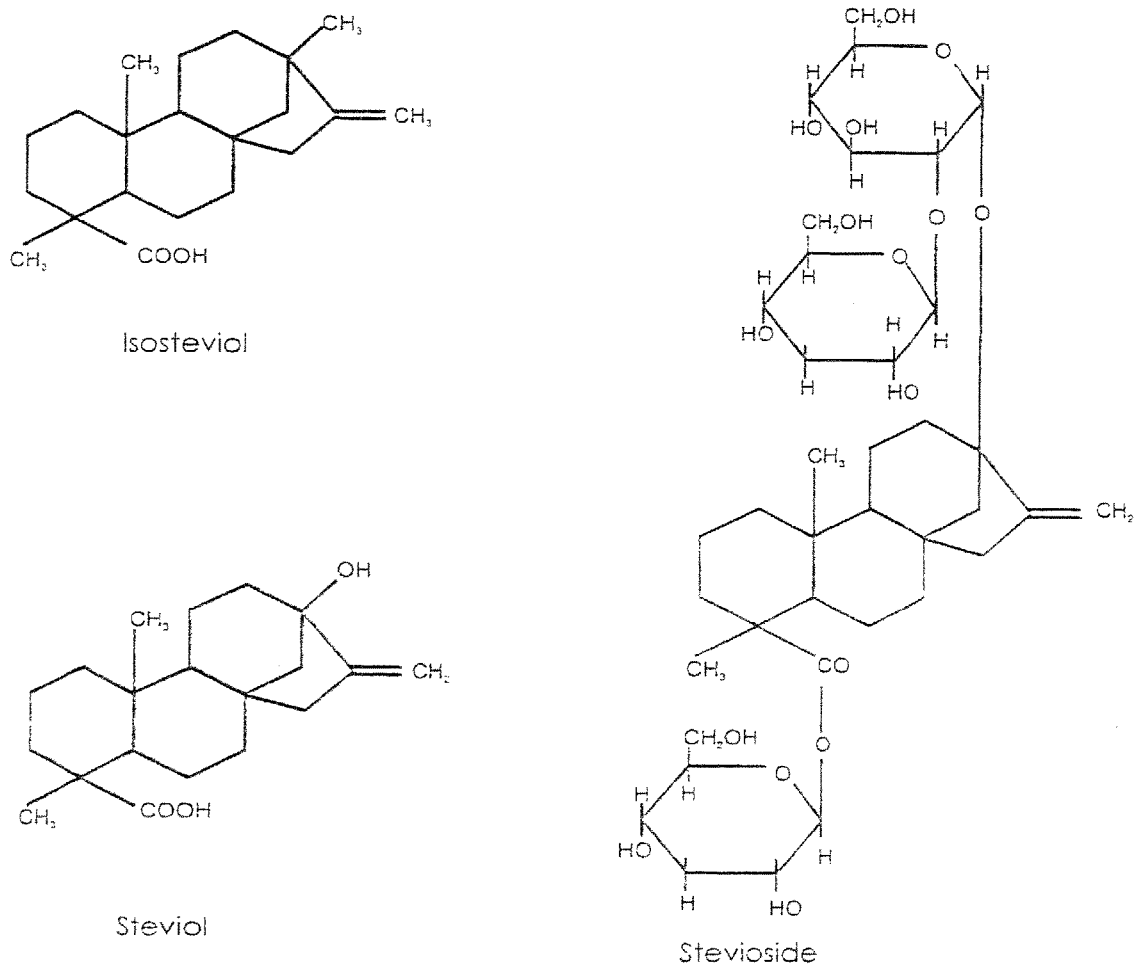
FIG. 1 shows the chemical structure of steviol, isosteviol and stevioside.
Figure 2A:
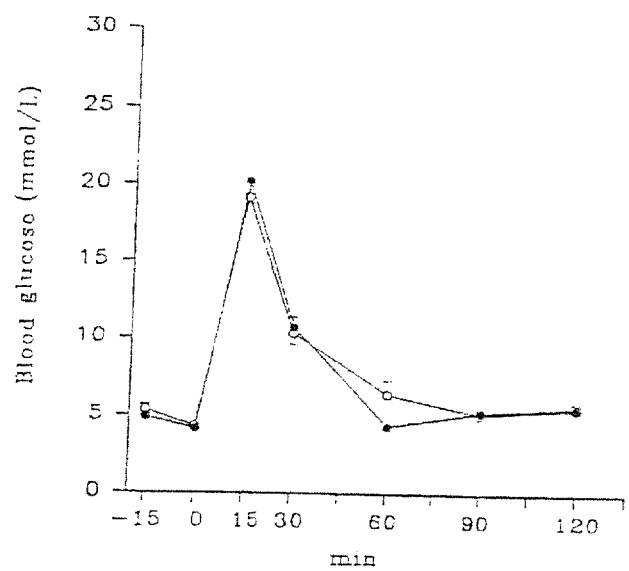
FIG. 2a shows the effect of stevioside on blood glucose during i.v. glucose tolerance test in normal Wistar rats.
Figure 2B:
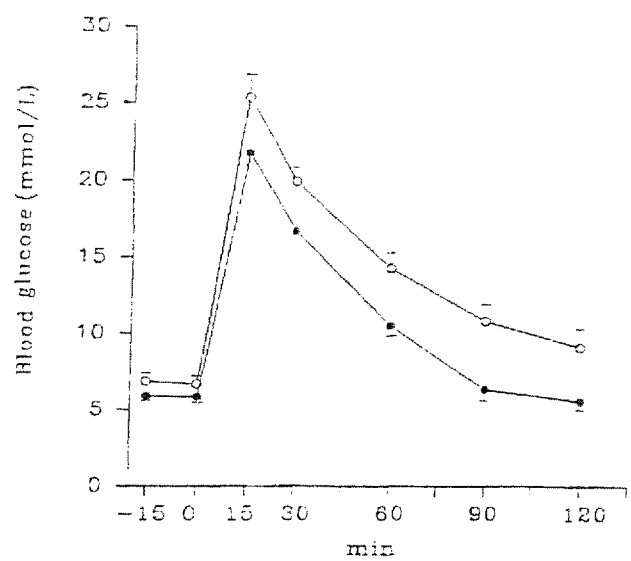
FIG. 2b shows the effect of stevioside on blood glucose during i.v. glucose tolerance test in GK rats.
Figure 3A:
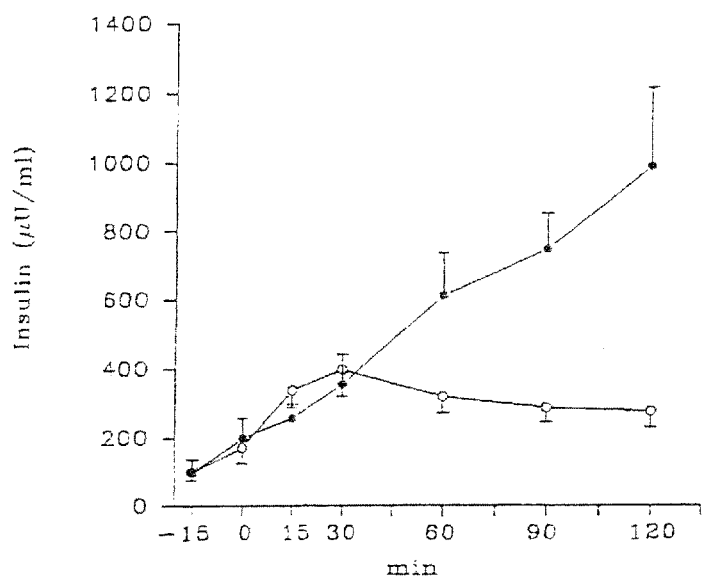
FIG. 3a shows the effect of stevioside on glucose-induced release during i.v. glucose tolerance test in normal Wistar rats.
Figure 3B:
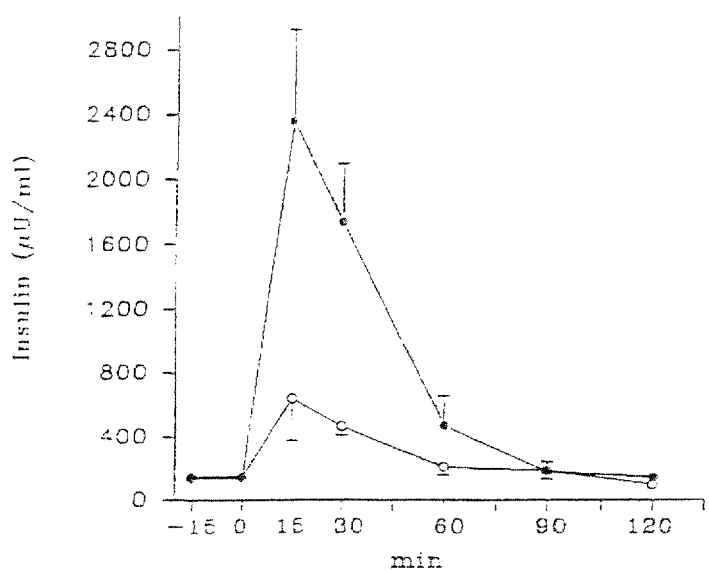
FIG. 3b shows the effect of stevioside on glucose-induced release during i.v. glucose tolerance test in GK rats.

Careful structural chemistry studies by the inventors have revealed that all potential substances for stimulating the insulin secretion extracted from the leaves of *Stevia rebaudiana* share the common unique skeletal structure of bicycle [3.2.1] octan of the formula I:

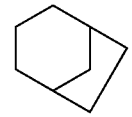

This bicyclo [3.2.1] octan can be found in e.g. steviol, isosteviol and in stevioside. The formula I structure has also been recognised in glucosilsteviol, gymnemic acid, steviolbioside, Rebaudioside A, Rebaudioside B, Rebaudioside C, Rebaudioside D, Rebaudioside E and Dulcoside A.

All these substances also share the common structure of formula II:

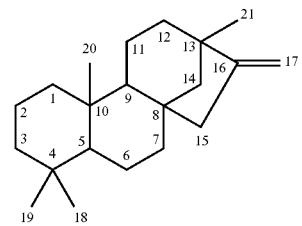

which is the basic structure in kaur-16-en-18-oic acid.

These specific structures of the formula I or II are recognized in several chemical compounds, which have been shown to have a highly potent insulin stimulating effect on isolated mouse pancreatic β-cell, and these structures of formula I and II are evidently the active parts of the molecules in causing the stimulating task.

This assumption is further confirmed by the fact that tests have shown that steviol having the smallest skeletal structure stimulate one insulin secretion to a greater extent than e.g. the glycoside stevioside having a much larger skeletal structure. Also, the inventors of the present invention have succeeded in purifying the different Rebaudiosides from *Stevia rebaudiana* and preclinical animal studies indicate the same stimulatory effect on insulin secretion.

Consequently this indicates that other compounds including the structures of the formula I or II, such as e.g. analogues, derivates and metabolites of the compounds mentioned above, can be used alternatively.

Studies and tests on rats have disclosed that the insulin stimulating effect of these substances is dependent on the concentration of the plasma glucose.

The substances comprising the chemical structures, which includes the formula I or II, did not cause an insulin release as long as the plasma glucose concentration was below approximately 6 mmol/l. At plasma glucose concentration above 6 mmol/l, the stimulating effect of the compounds provided an elevated plasma insulin concentration resulting in an immediate suppression of plasma glucose concentration thereby keeping this at a normal level.

In addition to the above findings, the present inventors have surprisingly found that the substances comprising the chemical structures including the formula I or II also have the capabilities of reducing the glucagon concentration in the blood.

This characteristic nature and qualities of the substances make them an obvious choice as a component in a medicament for the treatment of especially non-insulin dependent diabetes mellitus (NIDDM).

The finding that e.g. intravenously administered stevioside inhibited blood glucose responses to intravenous glucose in NIDDM rats (GK rats) but not in normal rats supports this fact. This finding is new and surprisingly has neither been expected nor demonstrated in earlier studies that have only been concerned with normal pancreatic islet cells.

As a further example of the unique action of the substances according to the invention, stevioside infusion at normal blood glucose did not cause any hypoglycemia irrespective of it being given as a bolus or at a constant intravenous infusion.

Due to the insulin secretory stimulating effect induced by a slightly elevated plasma glucose concentration, the simultaneous plasma glucagon reducing effect and the inhibited blood glucose response, these substances are able to control, regulate and adjust the plasma glucose concentration of a NIDDM patient to a normal level.

As a consequence of the glucose-dependency the substances only act when needed, e.g. after the patient has increased blood glucose after having eaten. In NIDDM patients treated with medicaments including these substances hypoglycemia will not occur and hypoglycemia will be counteracted.

Therefore, the substances provide a self-regulatory system responding only at elevated plasma glucose concentration.

The substances are preferably used in medicaments for oral medication. When taken orally, the glycosylated substances can be partially metabolised but the basic skeletal structure of the formula I or II will not be changed and the different characteristic effects mentioned above will be preserved.

The treatment with a medicament including these substances provides an attractive alternative to different types of drugs available and presently used today for the treatment of NIDDM, such drugs being drugs for stimulating the insulin secretion (sulphonylureas or repaglinide), drugs for improving the insulin sensitivity (biguanides and thiazolidinediones) or drugs for retarding gastrointestinal carbohydrate absorption (α-glucosidase inhibitors).

The potential of these new substances has for the first time also been tested in human NIDDM studies and the beneficial and advantageously combined multiple effects in humans of a single substance according to the invention has been demonstrated and will be further described in the examples.

The above-mentioned human tests have been conducted by orally administrating the substances, but within the scope of the invention the substances can optionally be used in the preparation of medicaments for intravenous, subcutaneous or intramuscular medication.

The substances further bring along the blood pressure reducing effect. In long-term experiments stevioside acutely suppresses blood pressure in diabetic rat. This important discovery is of the benefit to the diabetic patients that have developed hypertension in relation to or besides their disease.

When at least one of the substances according to the invention is combined in a medicament also comprising at least one soy protein alone or in combination with at least one isoflavone, it is possible to manufacture a combined preparation of a drug for the treatment of patients with the metabolic syndrome in accordance with the previously definition. Such a medicament may advantageously be used in prophylactic treatment of patient in a risk group. For example, a slow-release drug on the basis composition mentioned above provides a convenient treatment for the patient with the metabolic syndrome.

The inventors of the present invention have demonstrated that the combination of the substances according to the invention and at least one soy protein have a new unexpected and surprisingly synergistic effect surpassing the additive effect of the single components of the medicament thereby providing a completely new and very important medicament for therapeutic or prophylactic treatment of the metabolic syndrome.

The present inventors have used the combination of the substances according to the invention and at least one soy protein as a dietary supplementation in human studies. The test results significantly proved, as will be seen in the following examples, that such combination has a beneficial impact on cardiovascular risk markers in type II diabetic subjects.

Stevioside at a dose as high as 15 g/kg body weight was not lethal to either mice, rats or hamsters (Toskulkao C., Chaturat L., Temcharoen P., Glinsukon T. "Acute toxicity of stevioside, a natural sweetener, and its metabolite, steviol, in several animal species". Drug Chem. Toxicol. 1997 February-May; 20 (1-2), p. 31-44). In rats and mice, $LD_{50}$ values of steviol were higher than 15 g/kg body weight while the $LD_{50}$ for hamsters were 5-6 g/kg body weight. The latter was accompanied with degeneration of the proximal tubular cells, which correlated to increases in blood urea nitrogen and creatinine. Stevioside is excreted by the urine (Melis M. S. "Renal excretion of stevioside in rats". J. Nat. Prod. 1992 May; 55 (5), p. 688-90) and is not metabolised in the isolated perfused rat liver (Ishii-Iwamoto E. L., Bracht A. "Stevioside is not metabolised in the isolated perfused rat liver". Res. Commun. Mol. Pathol. Pharmacol. 1995 February; 87 (2), p. 167-75).

Stevioside and steviol showed no mutagenic effect on a number of *Salmonella typhirmurium* strains (Klongpanichpak S., Temcharoen P., Toskulkao C., Apibal S., Glinsukon T. "Lack of mutagenicity of stevioside and steviol in *Salmonella typhimurium* TA 98 and TA 100". J. Med. Assoc. Thai 1997 September; 80 Suppl. 1, p. 121-128; Suttajit M., Vinitketkaumnuen U., Meevatee U., Buddhasukh D. "Mutagenicity and human chromosomal effect of stevioside, a sweetener from *Stevia rebaudiana* Bertoni". Environ. Health Perspect 1993 October; 101 Suppl. 3, p. 53-56). In another study, it was confirmed that stevioside was not mutagenic whereas steviol, however, produced dose-related positive responses in some mutagenicity test (Matsui M., Matsui K., Kawasaki Y., Oda Y., Noguchi T., Kitagawa Y., Sawada M., Hayashi M., Nohmi T., Yoshihira K., Ishidate M. Jr., Sofuni T. "Evaluation of the genotoxicity of stevioside and steviol using six in vitro and one in vivo mutagenicity assays". Mutagenesis 1996 November; 11 (6), p. 573-579).

Stevioside is not carcinogenic in F344 rats (Toyoda K., Matsui H., Shoda T., Uneyama C., Takada K., Takahashi M. "Assessment of the carcinogenicity of stevioside.in F344 rats". Food Chem. Toxicol. 1997 June; 35 (6), p. 597-603). Doses as high as 2.5 g/kg body weight/day had no effect on growth or reproduction in hamsters (Yodyingyuad V., Bunyawong S. "Effect of stevioside on growth and reproduction". Hum. Reprod. 1991 January; 6 (1), p. 158-165).

To the knowledge of the inventors, no observations or reports showing potential toxic effects in humans have been published.

It will be recognised by the skilled artisan that rearranged structures of the formula II are within the scope of the invention, and such rearrangements might occur naturally in the gastro intestinal tract. As example can be mentioned that rearrangement may occur at the C16 forming a double bond to the C15 and thereby leaving a single bond open for substitution at position 17. A COOH group at position 18 is open for a number of reactions such as reaction with alcohol, as well as a number of substituents can be provided at any point of the formula II structure. Also, other substituents such as e.g. saccharides, at the various C-atoms and the structures may be anticipated.

EXAMPLES

In the following examples, the type II diabetic Goto-Kakizaki (GK) rats originated from Takeda Chemical Ind., Tokyo, Japan and were bred locally.

The normal Wistar rats and the NMRI mice were available from Bomholtgård Breeding and Research Centre Ltd., Ry, Denmark.

The rats had a weight of 300-350 g and the mice a weight of 22-25 g. The animals were kept on a standard pellet diet and tap water ad libitum.

The stevioside is obtained from the Japanese company WAKO-TriCHEM.

The abbreviation IAUC means Incremental Area Under the Curve (above basal).

Example 1

As examples of the effects of a compound including the chemical formulas II, stevioside was tested on normal Wistar rats and on GK rats. 2.0 g glucose/kg body weight and 0.2 g stevioside/kg body weight were dissolved in 0.9% saline and infused intravenously. The plasma glucose and insulin levels were measured over a period of 2 hours.

The results are shown in FIGS. 2a, 2b, 3a and 3b, were the O-O series (n=6 for Wistar and n=14 for GK) illustrate glucose infused alone and the ②-② series (n=6 for Wistar and n=12 for GK) illustrate the combined glucose and stevioside infusion. Data are given as mean±SEM.

After administration of the glucose load, plasma glucose raised immediately and plasma insulin raised abruptly. When stevioside was added together with the glucose, a diminished glucose response was found in the GK-rat and a significant decrease was observed already after 30 min. In the GK rat, stevioside caused a pronounced increase in the insulin response compared to the Wistar rat. The stevioside-induced insulin response was delayed and increased throughout the whole test. The insulin response was monophasic.

This discovery of stevioside having a blood glucose reducing effect in the type II diabetic rat indicates that stevioside and compounds having a similar chemical structure can be used in a medicament for the treatment of NIDDM in man.

Example 2

Islet from 6-10 NMRI mice were isolated and incubated in the presence of 16.7 mmol/l and $10^{-9}$-$10^{-3}$ mol/l stevioside or $10^{-9}$-$10^{-3}$ mol/l steviol.

Figure 4A:
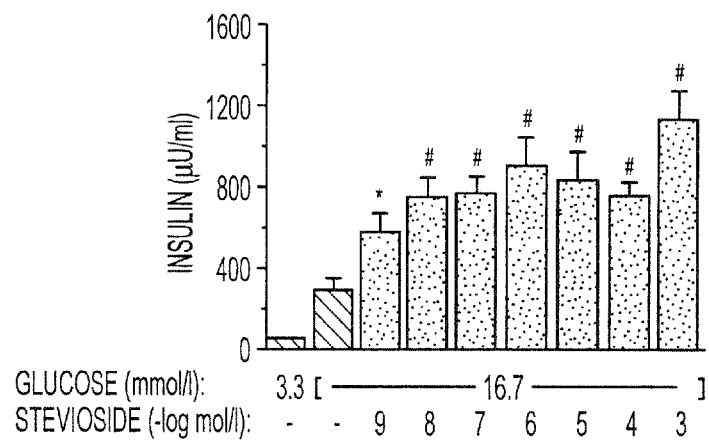
FIG. 4a shows the effect of stevioside on glucose-stimulated insulin secretion from isolated mouse islets.
Figure 4B:
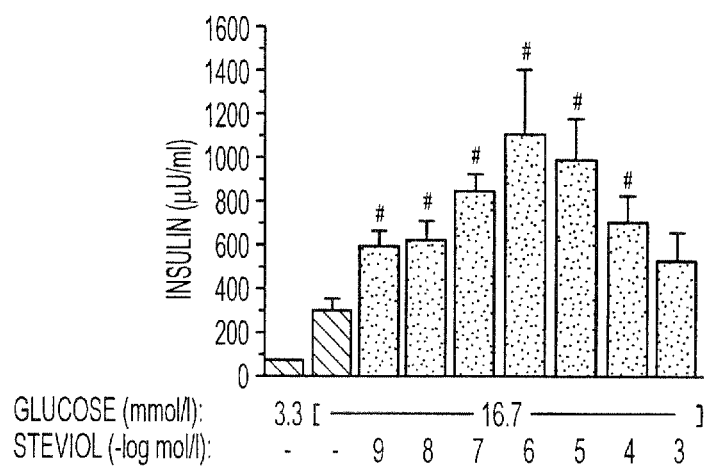
FIG. 4b shows the effect of steviol on glucose-stimulated insulin secretion from isolated mouse islets.

The results of these tests are illustrated in FIGS. 4a and 4b where each column represents mean±SEM from 24 incubations of single islets. Black bars in FIG. 4a indicate that stevioside is present and hatched bars indicate that stevioside is absent.

Black bars in FIG. 4b indicate that steviol is present and hatched bars indicate that steviol is absent.

The figures show that stevioside and steviol are capable of potentiating glucose-stimulated insulin secretion. Further tests confirmed that a stimulatory effect was found already at a very low concentration (above 0.1 nM).

Example 3

Figure 5A:
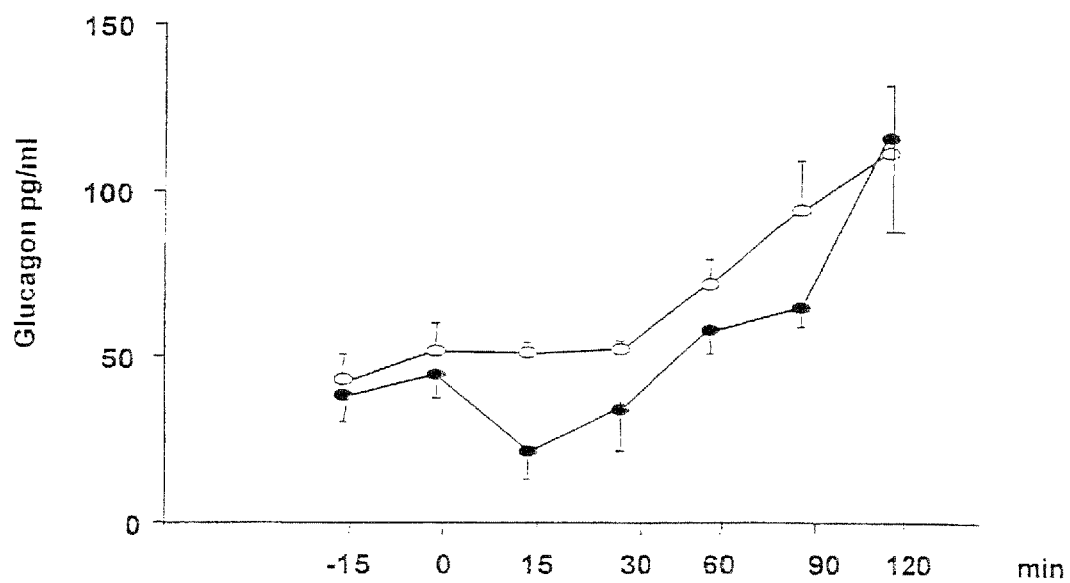
FIG. 5a shows the effect of an i.v. bolus injection of glucose on plasma glucagon levels during an intravenous glucose tolerance test in GK rats.

During a glucose tolerance test, an intravenous bolus of stevioside of 0.2 g/kg body weight was injected in GK rats (the ②-② serie (n=6)). GK rats receiving 0.9% saline intravenously served as controls (the O-O serie (n=6)). Glucose 2.0 g/kg body weight was administered as a bolus at timepoint 0 min. The plasma glucagon responses are shown as mean±SEM in FIGS. 5a (control) and 5b (GK). The plasma glucagon was suppressed in the stevioside treated GK rat.

Example 4

Figure 6A:
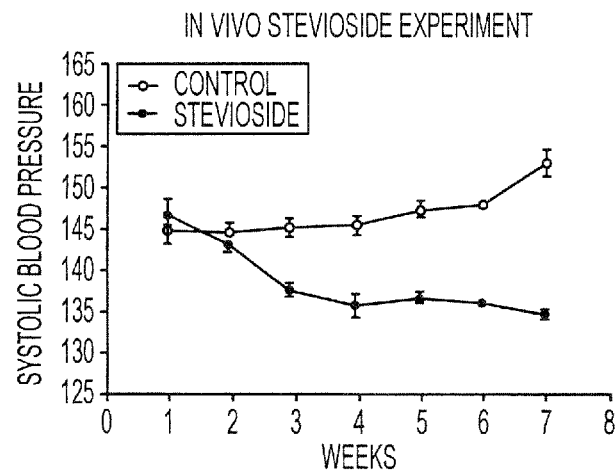
FIG. 6a shows the systolic blood pressure during 6 weeks treatment of GK rats with stevioside.
Figure 6B:
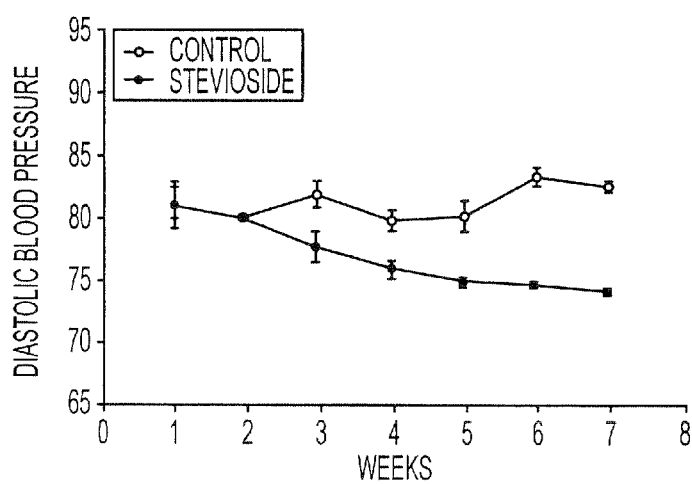
FIG. 6b shows the diastolic blood pressure in GK rats treated with stevioside.

GK rats were treated with stevioside 0.025 g/kg body weight/24 h for 6 weeks. Stevioside was administered in the drinking water. GK rats receiving drinking water with 0.111 g D-glucose/kg body weight/24 h served as controls. Systolic (FIG. 6a, control: O-O series, stevioside-treated: ②-② series) and diastolic (FIG. 6b, control: O-O series, stevioside-treated: ②-② series) blood pressures were measured on the tail.

The figures show a 10-15% decrease in the blood pressure detectable after 2 weeks of treatment and the effect hereafter was stable and consistent during the study period.

Example 5

Figure 7A:
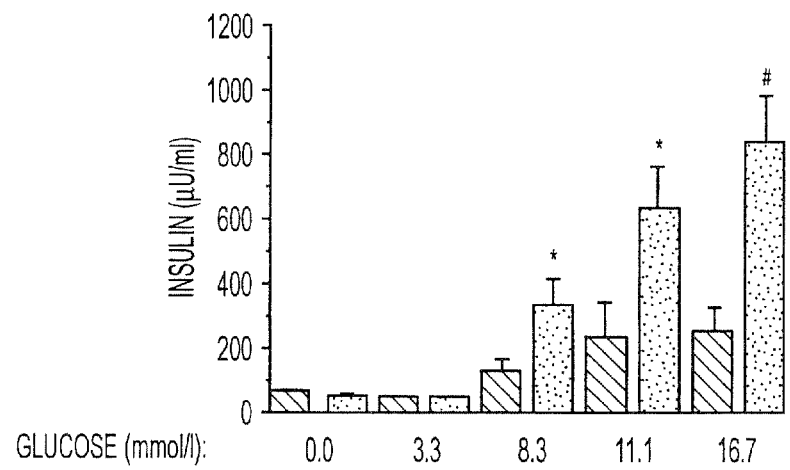
FIG. 7a shows the effect of $10^{-3}$ mmol/l stevioside on the insulin secretion from isolated mouse islets in the presence of glucose ranging between 0 and 16.7 mmol/l.
Figure 7B:
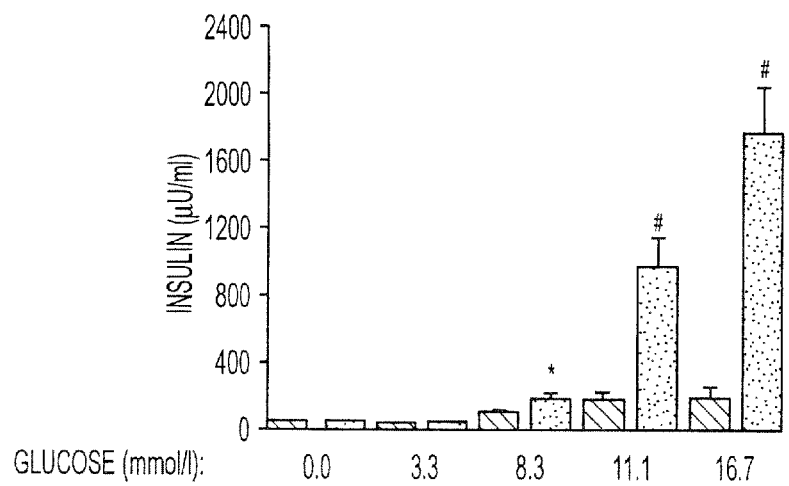
FIG. 7b shows the effect of $10^{-6}$ mmol/l steviol on the insulin secretion from isolated mouse islets in the presence of glucose ranging between 0 and 16.7 mmol/l, FIG. 8 a-d shows the acute effects of stevioside in type II diabetic patients.

The influence of the maximal stimulatory doses of $10^{-3}$ mol/l stevioside and $10^{-6}$ mol/l steviol was studied in NMRI mouse islets over a range between 0 and 16.7 mmol/l glucose. Both stevioside (FIG. 7a) and steviol (FIG. 7b) potentiated insulin secretion at and above 8.3 mmol/l and indicated that the initiating level for stimulating insulin secretion was between 3.3 mmol/l and 8.3 mmol/l of glucose. Black bars in FIG. 7a indicate that stevioside is present and hatched bars indicate that stevioside is absent. Black bars in FIG. 7b indicate that steviol is present and hatched bars indicate that steviol is absent.

Example 6

Twenty type II diabetic patients (6 female/14 males) with a mean age of 63.6±7.5 years participated in a controlled randomised double blind crossover trial. They were supplemented for 6 weeks with soy protein for (50 g/day) with high levels of isoflavones (minimum 165 mg/day) and cotyledon fibers (20 g/day) or placebo (casein 50 g/day) and cellulose (20 g/day) separated by a 3 week wash-out period.

This dietary supplement significantly reduced LDL-Cholesterol by 10% (p<0.05), LDL/HDL ratio by 12% (p<0.05), Apo B-100 by 30% (p<0.01), triglycerides by 22% (p<0.05) and homocystein by 14% (p<0.01). No change was observed in HDL-Cholesterol, Factor VIIc, von Willebrandt factor, fibrinogen, PAI-1, HbA1c or 24 hour blood pressure.

The results indicate beneficial effects of dietary supplementation with soy protein on cardiovascular risk markers in type II diabetic subjects. The improvement is also seen in individuals with near-normal lipid values. Ingestion of soy product has been shown to further improve the effectiveness of low-fat diets in non-diabetic subjects and the dietary supplementation in type II diabetic patients may provide an acceptable and effective option for blood lipid control, thereby postponing or even preventing drug therapy.

Example 7

Twelve type II diabetic patients (4 female/8 males) with a mean age of 65.8±1.6 years, a diabetes duration of 6.0±1.3 years, a mean body mass index of 28.5±1.0, and a mean glycated hemoglobin HbA1c of 7.4±0.4 percent were included in the study.

The experiment was an acute, paired, cross-over study in which two test meals were served during the experiments (A: Standard meal supplemented with 1 g of stevioside given orally; B: Standard meal given together with 1 g of gelatine (placebo) given orally. The total energy content of the test meals was 1725 kJ (protein 16 E %, fat 30 E %, carbohydrate 54 E %).

Blood samples were drawn from an antecubital vein 30 minutes before and 240 minutes after ingestion of the test meal. The arterial blood pressure was continuously monitored during the experiment. Students paired t-test was used for comparing the effects of stevioside with placebo on the parameters measured. Data are given as mean±SEM.

Figure 8A:
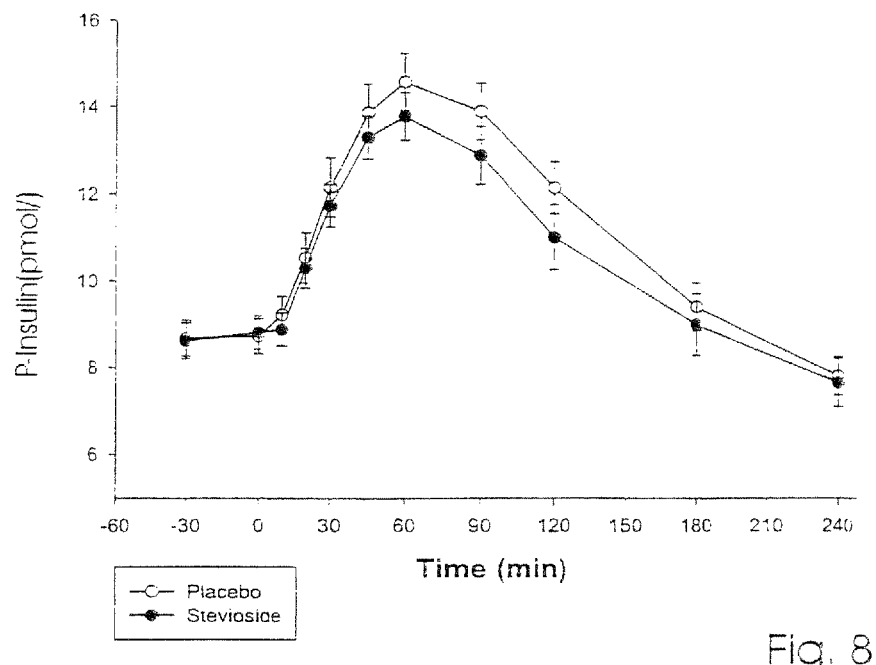
Figure 8B:
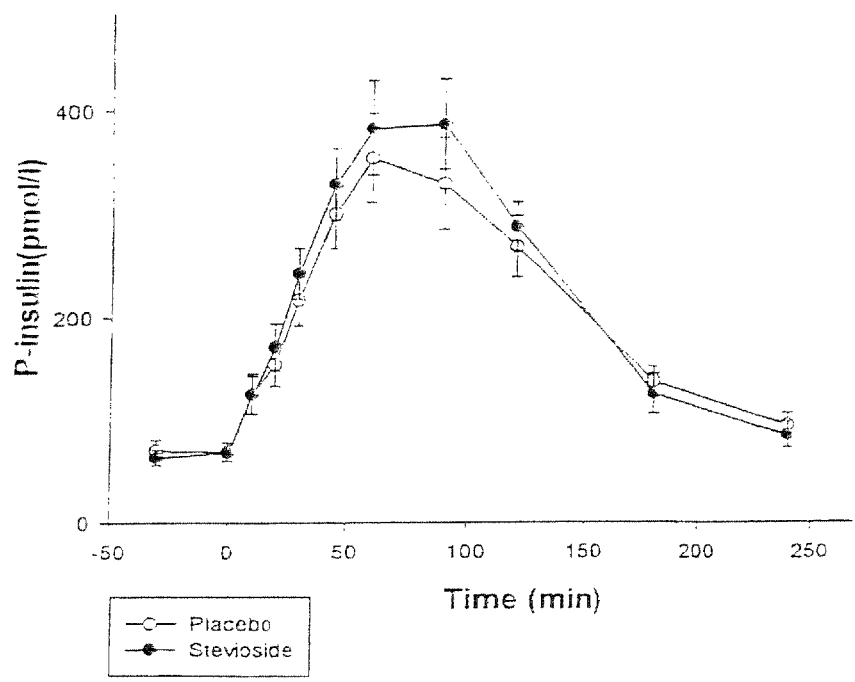

Stevioside reduced the postprandial blood glucose response by 18±5% (p<0.004) compared to placebo (absolute IAUC 638±55 vs. 522±64 mmol/l×240 min; p<0.02) as seen in FIG. 8a. Stevioside tended to stimulate the insulin response in type II diabetic patients (enhance the area under the insulin response curve (IAUC)), however the difference did not reach statistical significance (p=0.09) (FIG. 8b).

Figure 8C:
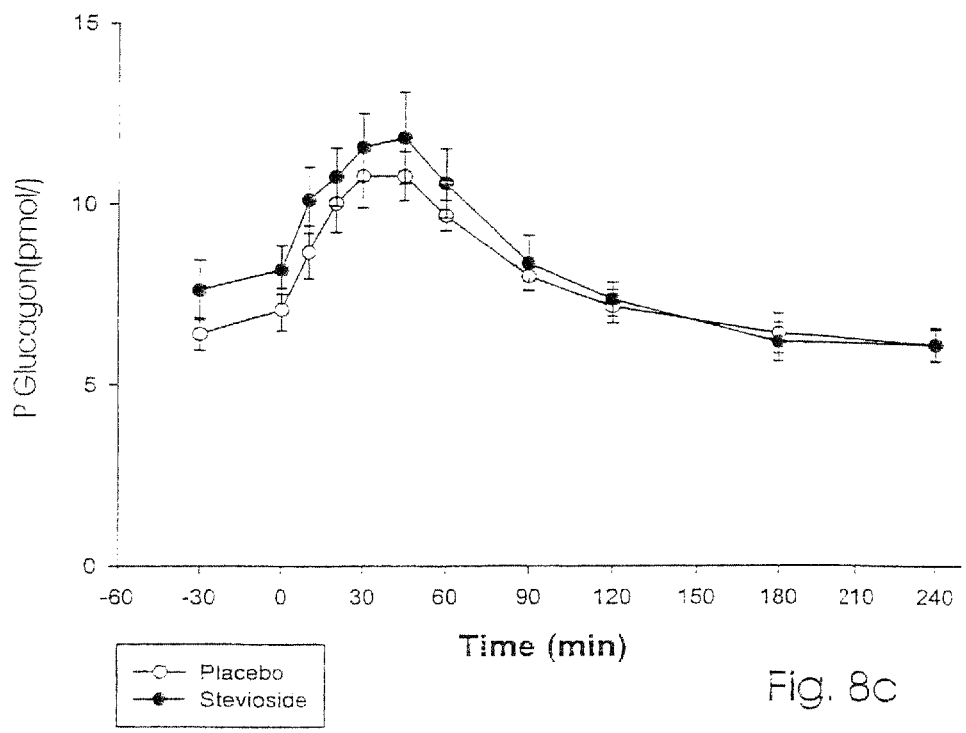

Stevioside significantly reduced the postprandial glucagon levels compared to placebo (348±46 vs. 281±33; p=0.02) (FIG. 8c).

Figure 8D:
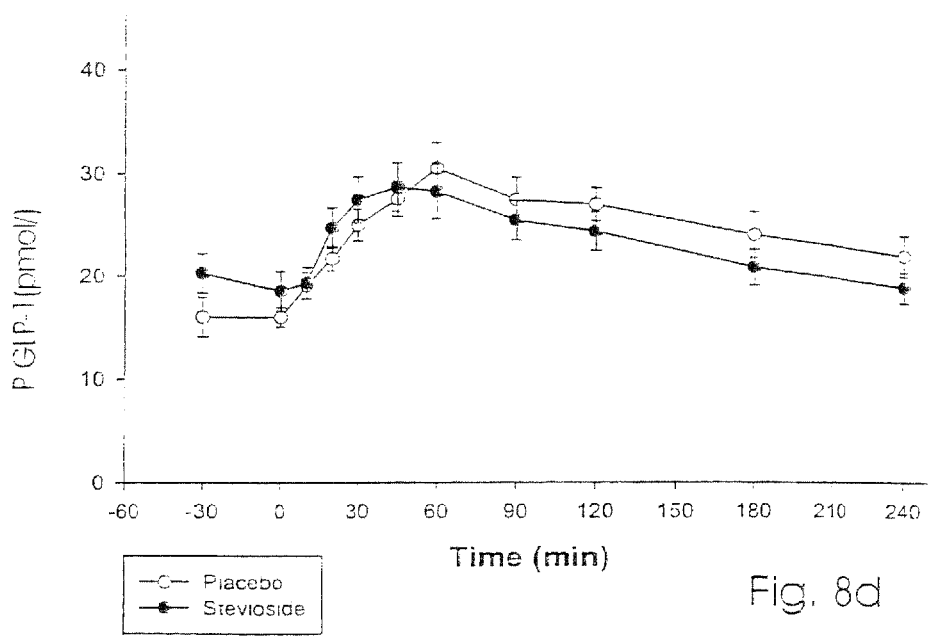

Stevioside significantly reduced the postprandial glucagon like peptide-1 (GLP-1) levels compared to placebo (2208±253 vs. 1529±296; p<0.045) (FIG. 8d).

Example 8

Four test diets (A: Standard carbohydrate rich laboratory animal diet (Altromin); n=12 (Alt). B: Altromin supplemented with stevioside (Altromin+Stevioside); n=12; (Alt+Ste). C: Soy plus 20% Altromin; n=12; (Soy). D: Soy plus 20% Altromin plus stevioside; n=12; (Soy+Ste)) were administered for four weeks to four groups of adult rats. Each experimental group consisted of twelve female Goto-Kakizaki wish an age of 9 weeks. The rats received the stevioside (0.025 g/kg body weight/day) with the drinking water. By the end of the third experimental week intra-arterial catheters were implanted into the carotid artery thereby enabling blood sampling during a 240 minutes glucose-tolerance test which was carried out by the end of the experiment at week 4. Blood samples were drawn after a bolus infusion of 2.0 g D-glucose/kg body weight. Plasma concentrations of glucose, insulin, and glucagon were measured during the glucose tolerance test. Immediately before the glucose tolerance test fasting levels of triglycerides and cholesterol were determined. Concomitantly, the systolic blood pressure was measured using a tail cuff.

Figure 9A:
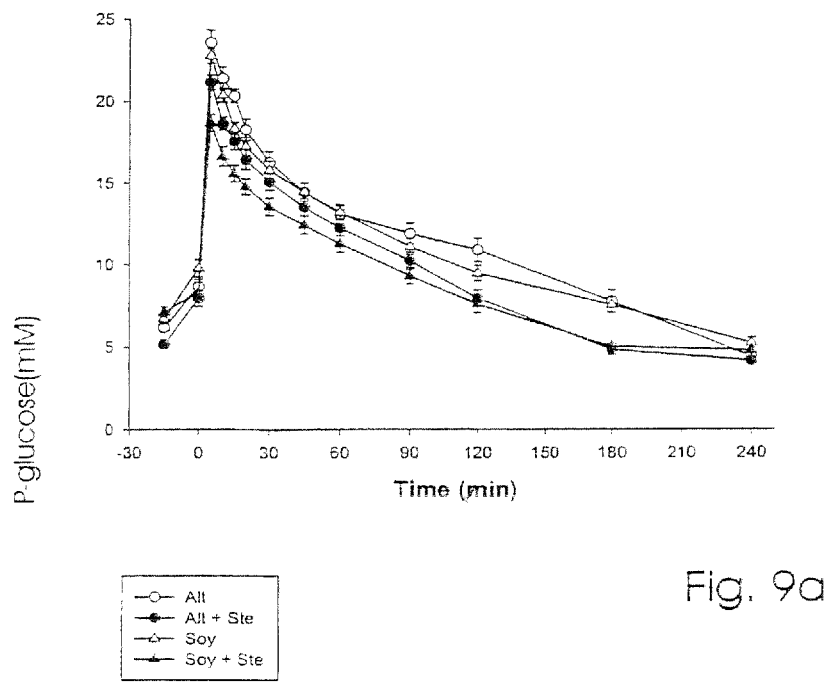
FIG. 9a-g shows the effects of the action of the combination of stevioside and soy based dietary supplementation in diabetic GK-rats.
Figure 9B:
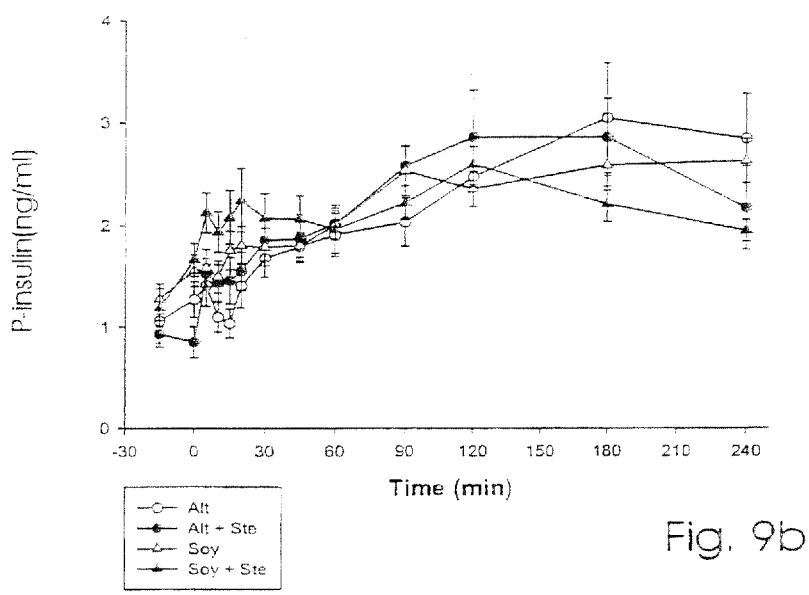

Effects on Plasma-Glucose:

As seen at FIG. 8 and in Table I below stevioside reduced the incremental area (IAUC) under the glucose response curve during the glucose tolerance testing both in the Altromin (p<0.05) and in the soy+20% Altromin group (Soy) (p<0.001). The relative effect of stevioside was more pronounced in the group receiving soy+20% Altromin group compared to the group receiving Altromin. The combination of soy and stevioside synergistically reduced the area under the glucose response curve compared to the Altromin group (p<0.0001) (FIG. 9a.).

(Plasma glucose was measured using MPR 3, 166 391, Glucose/GOD-PAP Method from Boehringer Mannheim)

Effects on Plasma Insulin:

The group receiving soy+stevioside (Soy+Ste) has reduced incremental area under the insulin response curve compared to the Altromin+stevioside group (Alt+Ste) as seen in FIG. 9 and in Table I below. Considering the concomitant blood glucose responses this indicates that soy increases the insulin sensitivity. Stevioside did not alter the insulin responses in the Altromin and soy diets when studying the total response curve from 0 to 240 minutes. However, in both groups supplementation of the diets with stevioside significantly improved the first phase insulin responses—which is subdued as a characteristic feature of type II diabetes. The combination of soy+stevioside synergistically improved the first phase insulin response (p<0.05) (FIG. 9b).

(Plasma insulin was measured using Sensitive Rat Insulin RIA, Cat #SRI-13K from Linco)

Figure 9C:
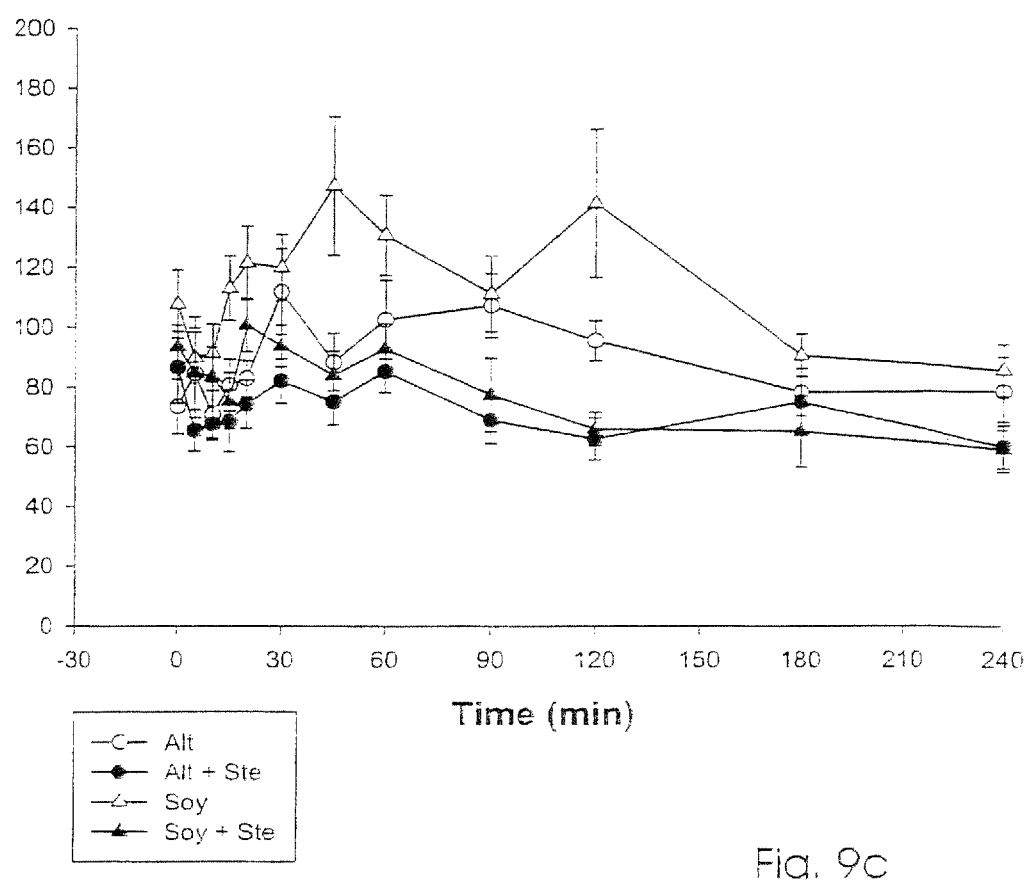

Effects on Plasma Glucagon:

Stevioside significantly reduced the area under the plasma-glucagon response curve during the glucose tolerance test in both the groups receiving Altromin (p<0.003) and soy (p<0.01) (see FIG. 9c and Table I below).

(Plasma glucagon was measured using Glucagon RIA. Cat #GL-32K from Linco)

Figure 9D:
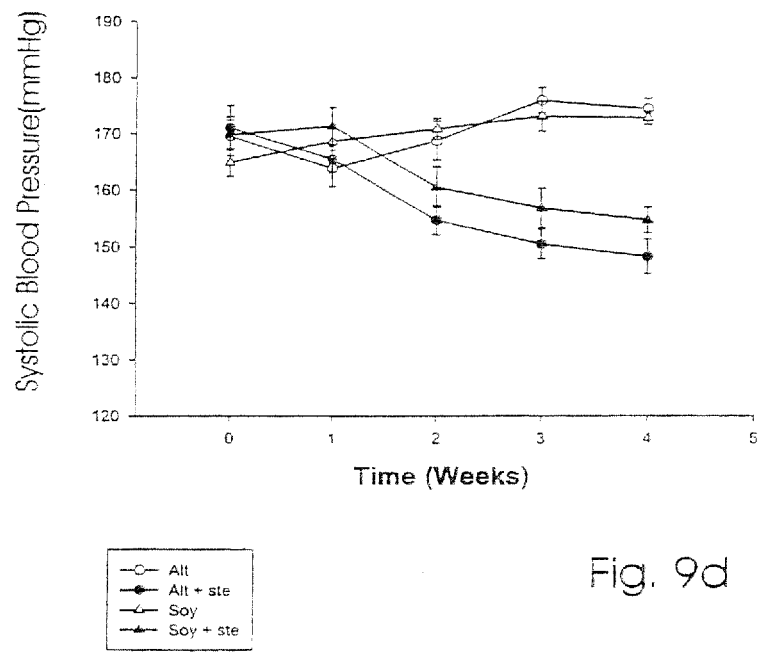

Effects on Blood Pressure:

A marked significant suppression of the systolic blood pressure (p<0.05) (Table I) is elicited by stevioside in combination with either Altromin (Δ=−28 mmHg) or soy (Δ=−21 mmHg) as depicted in FIG. 9d.

(Blood pressure was measured using TSE Non-Invasive Blood Pressure Monitoring System from Technical Scientific Equipment GmbK)

Figure 5B:
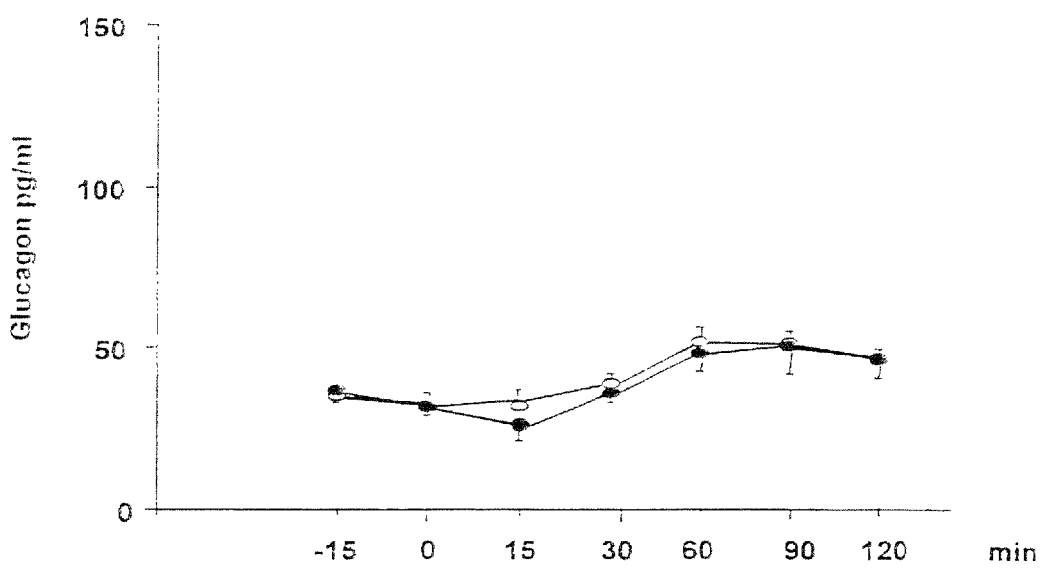
FIG. 5b shows the effect of an i.v. bolus injection of glucose and stevioside on plasma glucagon levels during a glucose tolerance test in GK rats.
Figure 9E:
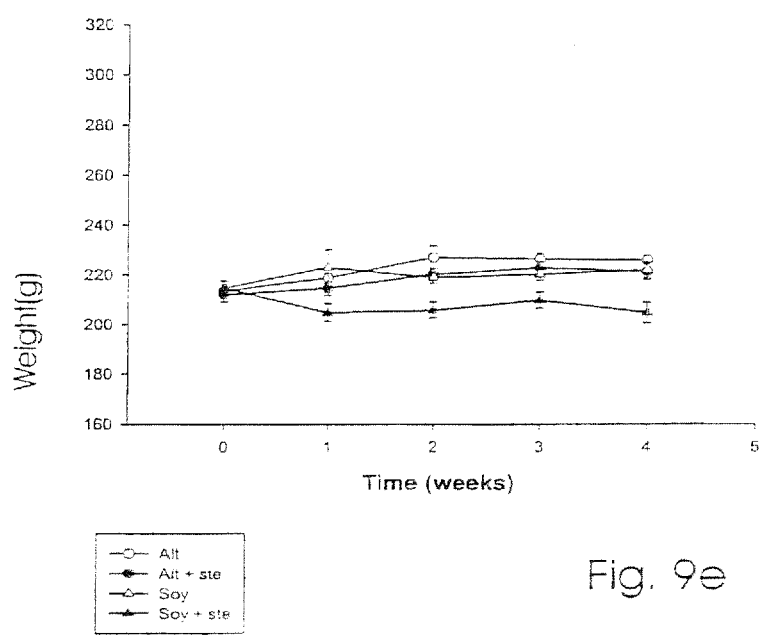
Figure 9F:
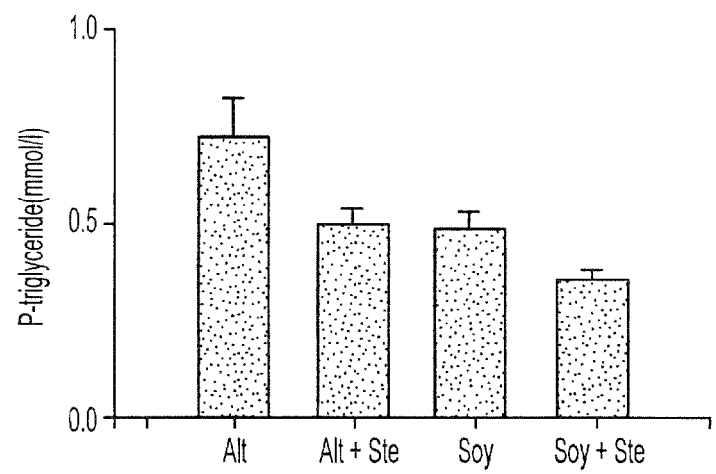
Figure 9G:
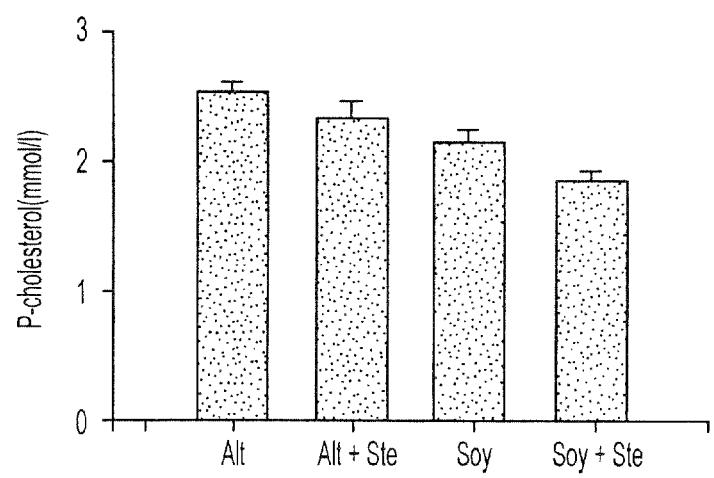

Effects on Body Weight:

The initial weights in the four groups did not differ (FIG. 5). Apparently the combination of soy and stevioside prevented weight gain as seen in FIG. 9e.

Effects on Triglyceride and Cholesterol:

Stevioside causes a significant suppression of the fasting triglyceride levels in combination with either Altromin (p<0.05) or soy (p<0.02) (Table I). Soy significantly reduced the fasting triglyceride levels with or without supplementation of stevioside (p<0.05 and p<0.002, respectively) (Table I). Stevioside given in combination with soy synergistically reduced the fasting total cholesterol levels compared to diets containing Altromin alone (p<0.0001). Soy alone also reduced the total cholesterol levels compared to Altromin alone (p<0.002) (FIG. 9f. and FIG. 9g) (Table I).

(Plasma cholesterol was measured GOD-PAP from Roche and triglycerides was measured using GHOD-PAP from Roche)

Stevioside exerts beneficial effects in type II diabetes i.e. reduces blood glucose, suppresses glucagon and improve first phase insulin secretion. The results also indicates that soy improves insulin sensitivity, a characteristic feature of the metabolic syndrome. Stevioside exerts a pronounced blood pressure reduction both with as well as without the presence of soy. The combination of stevioside and soy has a synergistic suppressive effect on blood glucose levels, enhances first phase insulin secretion, suppresses fasting plasma triglycerides and total cholesterol and the combination of soy and stevioside seems to prevent weight gain. The combination of stevioside and soy appears to possess the potential of an effective treatment of a number of the characteristic features of the metabolic syndrome i.e. type II diabetes, hypertension, dyslipidemia and obesity.

TABLE I

| Group | IAUC p-glucose (mM × 240 min) | IUAC p-insulin (ng/ml × 240 min) | IAUC p-insulin (ng/ml × 30 min) | IAUC p-glucagon (pg/ml × 240 min) | Change in blood pressure (mmHg) From week 0 to 4 | Triglycerides (mM) | Cholesterol (mM) |
|---|---|---|---|---|---|---|---|
| Altromin | 991 ± 96 | 317 ± 55 | 11 ± 4 | 21918 ± 1467 | 5 ± 4 | 0.72 ± 0.10 | 2.51 ± 007 |
| Altromin + Stevioside | 757 ± 53 | 375 ± 42 | 19 ± 4 | 17023 ± 1449 | −23 ± 6 | 0.50 ± 0.04 | 2.28 ± 0.18 |
| Soy + 20% Altromin | 820 ± 75 | 218 ± 22 | 9 ± 2 | 26200 ± 2410 | 8 ± 3 | 0.49 ± 0.04 | 2.13 ± 0.08 |
| Soy + 20% Altromin + Stevioside | 439 ± 56 | 248 ± 27 | 24 ± 5 | 17229 ± 1819 | −13 ± 5 | 0.37 ± 0.02 | 1.84 ± 0.06 |

Table I: Areas under the p-glucose, -insulin and -glucagon response curves during the glucose tolerance test in the four experimental groups. Change in systolic blood pressure at start and at end of the study period. Fasting plasma-triglyceride and -total cholesterol concentrations by the end of the study.

The invention claimed is:

1. A method of treating non-insulin dependent diabetes mellitus and/or the metabolic syndrome, said method comprises administering a substance selected from the group consisting of steviol and isosteviol to a patient in need thereof in a therapeutically effective amount.

2. The method according to claim 1, wherein the substance is steviol.

3. The method according to claim 1, wherein the substance is isosteviol.

4. The method according to claim 1, wherein the substance is isolated from a plant source.

5. The method according to claim 1, wherein the substances provides an insulin stimulating effect that is dependent on the plasma glucose concentration.

6. The method according to claim 5, wherein the plasma glucose concentration is above 6 mmol/l.

7. The method according to claim 1, wherein the substance controls, regulates and adjusts the plasma glucose concentration to a normal level in a non-insulin dependent diabetes mellitus patient.

8. The method according to claim 1, wherein at plasma glucose concentrations above 6 mmol/l, the treatment provides an elevated plasma insulin concentration resulting in an immediate suppression of the plasma glucose concentration thereby keeping this at a normal level.

9. The method according to claim 1, wherein the treatment is a stimulation of the insulin secretion in a mammal afflicted with non-insulin dependent diabetes mellitus, wherein the stimulation of the insulin secretion is initiated by the presence of a plasma glucose concentration of 6 mmol/l or larger.

10. The method according to claim 1, wherein the substance is administered orally.

11. The method according to claim 1, wherein the substance is administered intravenously, subcutaneously or intramuscularly.

12. The method according to claim 1, wherein the substance is administered in combination with at least one soy protein or in combination with at least one isoflavone.

13. The method according to claim 1, wherein the substance is administered in combination with at least one soy protein.

* * * * *